(12) United States Patent
Van Zant et al.

(10) Patent No.: US 8,110,184 B2
(45) Date of Patent: Feb. 7, 2012

(54) EX VIVO AND IN VIVO METHODS AND RELATED COMPOSITIONS FOR GENERATING HEMATOPOIETIC STEM CELL POPULATIONS

(75) Inventors: Gary Van Zant, Lexington, KY (US); Ying Liang, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 1528 days.

(21) Appl. No.: 11/540,641

(22) Filed: Oct. 2, 2006

(65) Prior Publication Data
US 2007/0116681 A1 May 24, 2007

Related U.S. Application Data

(60) Provisional application No. 60/722,755, filed on Sep. 30, 2005.

(51) Int. Cl.
*A61K 35/14* (2006.01)
*C12N 5/08* (2006.01)
(52) U.S. Cl. ...................... 424/93.7; 435/372
(58) Field of Classification Search .................... None
See application file for complete search history.

(56) References Cited

U.S. PATENT DOCUMENTS
5,998,373 A * 12/1999 Hillman et al. .............. 514/20.1

OTHER PUBLICATIONS

Ying Liang, PhD Dissertation (1995).*
Ying Liang, PhD Dissertation. University of Kentucky (2005). Genetic Regulation of Hematopoietic Stem Cell Numbers in Mice.*

* cited by examiner

*Primary Examiner* — Scott Long
(74) *Attorney, Agent, or Firm* — Crowell & Moring LLP

(57) ABSTRACT

Various embodiments provide methods and related compositions for increasing the population size of hematopoietic stem cells (HSCs) in patients that may benefit from reconstitution of stem cells and/or differentiated cells of the blood lineage. The present methods enable the production of HSCs ex vivo and in vivo by reducing latexin expression and/or latexin activity within HSC exposed to various antagonists. Inhibition of latexin expression and/or latexin activity by various antagonists can promote HSC proliferation and/or inhibit HSC apoptosis. Antagonists that can reduce latexin expression and/or latexin activity can be utilized to regenerate endogenous HSCs within patients affected with disorders, diseases, cancers, or therapies for such conditions, that result in the depletion or reduction in HSCs.

17 Claims, 16 Drawing Sheets

| LRS | Chromosome Location (Mb) | Locus | Additive Effects |
|---|---|---|---|
| 10.640 | 3 (56.96) | mCV22953681 | − 0.163 |
| 10.640 | 3 (57) | rs13477128 | − 0.163 |
| 10.640 | 3 (57.46) | rs363066 | − 0.163 |
| 10.640 | 3 (57.64) | Gnf03.054.694 | − 0.163 |
| 10.640 | 3 (58.1) | rs6301139 | − 0.163 |
| 10.640 | 3 (60.9) | CEL-3_59198871 | − 0.163 |
| 14.379 | 3 (61.8) | rs13477144 | − 0.183 |
| 14.379 | 3 (62.2) | rs13477148 | − 0.183 |
| 14.379 | 3 (65.0) | rs6191597 | − 0.183 |
| 14.379 | 3 (65.3) | rs13459069 | − 0.183 |
| 11.436 | 3 (66.1) | rs3674751 | − 0.167 |
| 11.436 | 3 (66.1) | rs13477166 | − 0.167 |
| 11.436 | 3 (66.2) | D3Mit241 | − 0.167 |
| 11.436 | 3 (66.3) | Gnf03.063.824 | − 0.167 |
| 11.436 | 3 (66.8) | rs13477169 | − 0.167 |

US 8,110,184 B2

EX VIVO AND IN VIVO METHODS AND RELATED COMPOSITIONS FOR GENERATING HEMATOPOIETIC STEM CELL POPULATIONS

CROSS-REFERENCES

This application is a non-provisional application that claims priority under 35 U.S.C. §119 to U.S. Provisional Application No. 60/722,755 entitled MANIPULATION OF ADULT STEM CELL POPULATION SIZES BY LATEXIN and filed on Sep. 30, 2005, the entire content of which is hereby incorporated by reference.

STATEMENT OF GOVERNMENT INTEREST

This invention has been made with Government support under grant number ROI AG024950, awarded by the National Institute on Aging. The government has certain rights in the invention.

TECHNICAL FIELD

The present invention relates to methods for regenerating adult hematopoietic stem cells (HSCs) and related compositions by reducing/inhibiting latexin expression and/or latexin activity.

INCORPORATION-BY-REFERENCE & TEXTS

The material on the accompanying CD-R is hereby incorporated by reference into this application. The accompanying compact disc contains one file, 1028750-000249 HSCS.ST25.txt, which was created on Oct. 2, 2006. The file named 1028750-000249 HSCS.ST25.txt is 5 KB. The file can be accessed using Microsoft Word on a computer that uses Windows OS.

BACKGROUND OF THE INVENTION

Hematopoiesis is a complex process for producing multiple and distinct lineages of blood-borne cells throughout the life span of an organism. Hematopoietic stem cells ("HSCs") represent a subset of undifferentiated cells that resides predominantly in the bone marrow of adult mammals. HSCs, as a population, are capable of self-renewal by maintaining a sufficient number of HSCs within an organism's bone marrow as a reservoir of uncommitted cells that can be further differentiated into various types of new blood cells. Such newly generated blood cells emerge from the bone marrow and enter the circulatory system in order to continuously replace mature/aging circulating blood cell types. The ability of HSCs, as a population, to differentiate and to give rise to cells of multi-lineages is critical for the preservation of an organism.

In order for the maintenance of steady-state hematopoiesis, a balance must be achieved between the rate of self-generation (i.e., for maintaining a steady supply of HSCs) and the rate of differentiation (i.e., for replenishing senescent cells). Hematopoiesis occurs as a developmental continuum in that a given population of HSCs is representative of a heterogeneous mixture of cells, mainly composed of long-term HSCs ("LT-HSCs") and short-term HSCs ("ST-HSCs"). LT-HSCs are stem cells that have the capacity for self-renewal throughout the life span of an organism. However, ST-HSCs exhibit transient self-renewal properties for a limited period of time (e.g., typically less than 8 weeks in a mouse) prior to undergoing full differentiation. HSCs can differentiate into hematopoietic progenitor cells ("HPCs") that can further differentiate into clonogenic cells, or cells of a single lineage. For example, the differentiation of common lymphoid progenitors ("CLPs") can produce T lymphocytes ("T cells"), B lymphocytes ("B cells"), and natural killer cells ("NKs"). The differentiation of common myeloid progenitors ("CMPs") can generate blood cells of other lineages, including erythrocytes, macrophages, granulocytes, and platelets. The maintenance of mature blood-borne cells in the peripheral circulation is critical for various processes, including oxygen delivery and immunological protection.

Bone marrow transplantation ("BMT") and hematopoietic stem cell transplantation ("HSCT") can be effective for the treatment of diseases of the blood, diseases of the bone marrow, cancers of the blood, and cancers of the bone marrow, including various types of anemia, leukemia, and immunological disorders. For example, obtaining HSCs by bone marrow harvesting from donors can be technically challenging in that harvesting sufficient material from the bone marrows of donors involves multiple insertions of large needles to obtain sufficient amount of stem cells. Methods for regenerating HSCs can be useful for treating patients affected by various types of disorders, diseases, or cancers that deleteriously affect the number of endogenous HSCs within a patient.

SUMMARY OF THE INVENTION

An ex vivo method for producing a renewed population of hematopoietic stem cells (HSCs) is provided, in which a first HSC population from a donor is obtained, the first HSC population is contacted with an antagonist that reduces latexin expression and/or latexin activity, and the HSC population is cultured under in vitro conditions that can promote cell proliferation and/or inhibit apoptosis to obtain a second HSC population that comprises a progeny of the first HSC population.

A method for reconstituting a recipient host with a HSC population generated ex vivo is provided, in which a first HSC population from a donor is obtained, the first HSC population is contacted with an antagonist that reduces latexin expression and/or latexin activity, the HSC population is cultured under in vitro conditions that can promote cell proliferation and/or inhibit apoptosis to obtain a second HSC population that comprises a progeny of the first HSC population, and the second HSC population is transplanted to the recipient host in need of HSC reconstitution.

A method for reconstituting a recipient host with a HSC population generated in vivo is provided, in which the recipient host is administered with a pharmaceutical composition comprising an antagonist that reduces latexin expression and/or latexin activity.

DETAILED DESCRIPTION OF THE INVENTION

Figure 1:
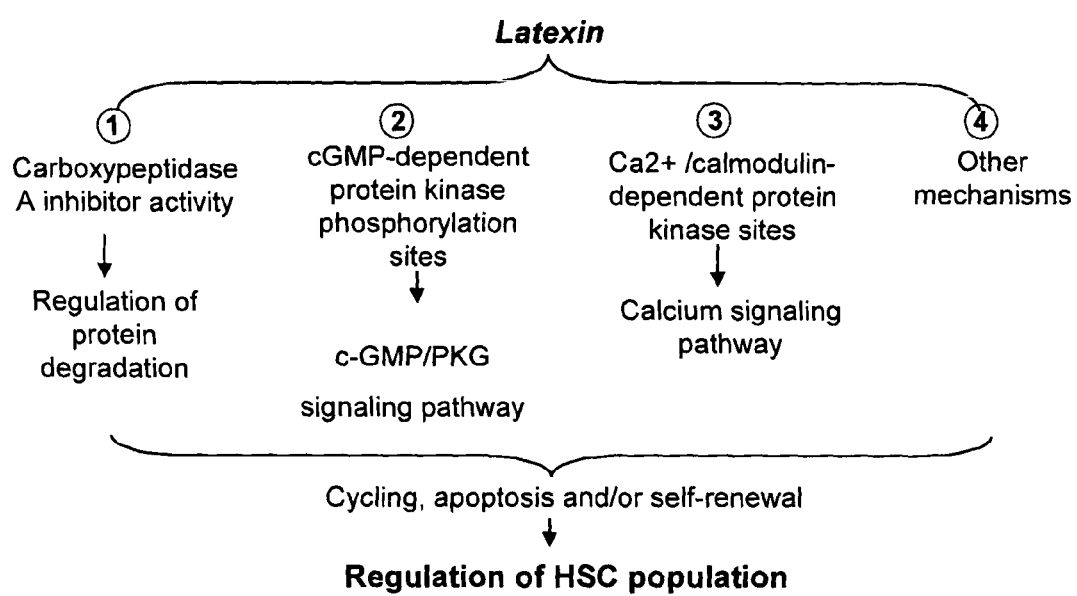
FIG. 1 illustrates various biochemical pathways mediated by latexin that may be involved in the regulation of HSC proliferation in mammals, as described in Example 1.

Various embodiments provide methods and related compositions useful for reconstituting hematopoietic stem cells (HSCs) within a patient in need of HSC renewal. For example, the present methods are useful for the treatment of patients affected with disorders, diseases, and/or cancers that deleteriously compromise the number of endogenous HSCs and differentiated forms of such HSCs within patients. Examples of disorders, diseases, and/or cancers contemplated for treatment by the present methods and compositions include diseases of the blood, diseases of the bone marrow, cancers of the blood, and cancers of the bone marrow, including various types of anemia, leukemia, immunological disorders, thalassemia major, sickle-cell disease, myelodysplastic syndrome, lymphoma, aplastic anemia, and multiple myeloma. Patients that may benefit from treatments that utilize the present methods and related compositions include candidates for bone marrow transplantation ("BMT") and hematopoietic stem cell transplantation ("HSCT"). Transplantation therapies can be effective for the treatment of various types of leukemia and any disorder/disease/cancer for which patients are subjected to radiotherapy and/or chemotherapy. The renewed or regenerated population of HSCs that can be induced by the present methods and compositions are useful for various applications, including regenerative medicine, tissue engineering, tissue repair, cancer therapy, and gene therapy. As described in the following embodiments, a given HSC population obtained from a donor or within a recipient host (i.e., a patient) can be induced to proliferate and/or to suppress apoptosis by providing antagonistic compounds/compositions that can inhibit latexin expression and/or latexin activity.

I. Definitions

As used throughout the specification and the appended claims, the terms listed below have the following meanings, wherein "a" means one or more:

The terms "hematopoietic stem cells" ("HSCs") refer to a heterogeneous mixture of undifferentiated progenitor stem cells, mainly composed of long-term HSCs ("LT-HSCs") and short-term HSCs ("ST-HSCs"). LT-HSCs are undifferentiated stem cells that have the capacity for self-renewal throughout the life span of an organism. ST-HSCs are undifferentiated stem cells that have the capacity for self-renewal for a limited time prior to full differentiation into a specific lineage. For example, HSCs can differentiate into hematopoietic progenitor cells ("HPCs") that can further differentiate into clonogenic cells, or cells of a single lineage, that represent a subset of a hematopoietic lineage. HSCs include non-embryonic stem cells isolated from post-natal animals. HSCs include "pluripotent adult stem cells" isolated from the bone marrows of mammals that are capable of differentiating into tissues of all three germ or dermal layers, such as the mesoderm, endoderm, and ectoderm. A "pluripotent stem cell" refers to a stem cell that exhibits the capacity to grow into any type of cell that constitutes an organism. A pluripotent cell can be self-renewing and can remain dormant/quiescent within a tissue. HSCs include "multipotent stem cells" that exhibit the capacity to grow into any subset of cells that constitute an organism. HSCs include undifferentiated stem cells that exhibit a distinct profile of cell surface markers, including the following combination of markers: Thy-$1^{lo}$ Sca-$1^+$ Lineage$^-$ c-kit$^+$; or CD $150^+$ CD48$^-$ Sca-$1^+$ Lineage$^-$ c-kit$^+$; or Thy-$1^{lo}$ CD150$^+$ CD48$^-$ Sca-$1^+$ Lineage$^-$ c-kit$^+$ (Kiel et al., Cell, Vol. 121, p 1109-1121 (2005)). HSCs that express the combination of human counterparts for these markers are preferably contemplated. The following references are herein incorporated by reference in their entirety: Cheshier et al., P.N.A.S., Vol. 96, p 3120-3125 (1999); Eckfeldt et al., Nature, Vol. 6, p 726-737 (2005); Wright et. al., Science, Vol. 94, p 1933-1936 (2001); and Preston et al., J. Clin. Pathol. Vol. 56, p 86-96 (2003).

The term "first HSC population" refers to HSCs obtained from a donor, wherein the first HSC population expresses cell surface markers as described supra.

The term "second HSC population" refers to the progeny of the first HSC population produced by in vitro cell proliferation under in vitro conditions, wherein the second HSC population expresses cell surface markers as described supra.

The term "latexin" ("Lxn") refers to the Lxn gene, isoforms/variants of the Lxn gene, and gene products derived from the Lxn gene, including messenger RNA and protein. The sense-strand of a human latexin cDNA is provided as SEQ ID NO:1. A human latexin protein sequence is provided as SEQ ID NO:2. Latexin isoforms/variants include genes containing exon sequences having at least about 70%, 75%, 80%, 85%, 90%, 95%, 96%, 97%, 98%, or 99% sequence similarity to SEQ ID NO:1; genes containing exon sequences having at least about 70%, 75%, 80%, 85%, 90%, 95%, 96%, 97%, 98%, or 99% sequence identity to SEQ ID NO:1; those sequences encoded by genes containing exon sequences having at least about 70%, 75%, 80%, 85%, 90%, 95%, 96%, 97%, 98%, or 99% sequence similarity to SEQ ID NO:1; those sequences encoded by genes containing exon sequences having at least about 70%, 75%, 80%, 85%, 90%, 95%, 96%, 97%, 98%, or 99% sequence identity to SEQ ID NO:1; those sequences having at least about 70%, 75%, 80%, 85%, 90%, 95%, 96%, 97%, 98%, or 99% sequence similarity to SEQ ID NO:2; and those sequences having at least about 70%, 75%, 80%, 85%, 90%, 95%, 96%, 97%, 98%, or 99% sequence identity to SEQ ID NO:2. Latexin isoforms/variants include mammalian homologs listed in Tables 1-3. Examples of latexin isoforms/variants include the carboxypeptidase inhibitor (CARIN) described in U.S. Pat. No. 5,998,373.

The term "antagonist" refers to any compound or composition that can inhibit the expression and/or the activity of latexin and latexin isoforms, including sequence-specific polynucleotides that can interfere with the transcription of endogenous latexin gene; sequence-specific polynucleotides that can interfere with the translation of latexin mRNA transcripts (e.g., siRNAs, ribozymes); sequence-specific polypeptides that can interfere with the protein stability of latexin, the enzymatic activity of latexin, and/or the binding activity of latexin with respect to substrates and/or regulatory proteins; and small molecule compounds that can interfere with the protein stability of latexin, the enzymatic activity of latexin, and/or the binding activity of latexin. An effective antagonist can promote HSC proliferation by at least 25%, 30%, 35%, 40%, 45%, 50%, 55%, 60%, 65%, 70%, 75%, 80%, 85%, 90%, 95%, or 100%. An effective antagonist can suppress HSC apoptosis by at least 25%, 30%, 35%, 40%, 45%, 50%, 55%, 60%, 65%, 70%, 75%, 80%, 85%, 90%, 95%, or 100%.

II. Regulation of Cell Cycling, Apoptosis and Proliferation of Hematopoietic Stem Cells (HSCs) Mediated by Latexin The present inventors have identified a quantitative trait loci ("QTL") that confers variation in HSC numbers in young and adult C57BL/6 (B6) and DBA/2 (D2) mice. By utilizing reciprocal Chromosome 3 congenic mice derived from these two parental strains, such as B.D Chr3 and D.B Chr3 mice, the present inventors have demonstrated that introgressed D2 alleles confer an increase in HSC population size by enhancing HSC cell proliferation (i.e., HSC self-renewal) and/or by suppressing HSC apoptosis, as seen in B.D Chr3 congenic mice. In contrast, the B6 alleles conferred a decrease in HSC population size. Differential expression levels conferred by these alleles correlated with the latexin ("Lxn") gene locus. Differential latexin expression levels were shown to inversely correlate with HSC population size, based on experimental data obtained utilizing oligonucleotide arrays (e.g., microarrays), real-time PCR, and Western blots. Ectopic expression of latexin protein from a retroviral construct resulted in a decrease in stem cell population size. Clusters of single nucleotide polymorphisms (SNPs) were identified upstream of the Lxn transcriptional start site. At least two of these clusters appear to be associated with potential binding sites for transcription factors involved in hematopoietic stem cell regulation. Thus, promoter polymorphisms between B6 and D2 alleles appear to affect Lxn gene expression, and consequently, to influence HSC population size. The results of these experiments are presented in FIGS. 1-9 and are further described in Examples 1-15.

Latexin was identified initially as an antigen expressed within the rat cerebral cortex. Latexin mRNA and protein (29 kDa) have been shown by others to be expressed in neural and non-neural tissues. Latexin exhibits inhibitory activity against rat carboxypeptidase A1 ("CPA1"), carboxypeptidase A2 ("CPA2"), and mast-cell CPA (Uratani et al., Biochem. J., Vol 346: 817-826 (2000). CPA and CPB are pancreatic zinc-containing proteolytic enzymes that catalyze the hydrolysis of the carboxyl-terminal peptide bond within polypeptide chains. Carboxypeptidase activities can be regulated either by endogenous protein inhibitors or by enzymatic cleavage of a segment of a propeptide that releases the active form of the carboxypeptidase. Both latexin and Tissue Carboxypeptidase Inhibitor (TCI) are examples of endogenous protein inhibitors of carboxypeptidases. Latexin and TCI contain several potential phosphorylation sites, and both are expressed and localized in the cytosol of a number of tissues, including the brain, the lung, and the digestive tract.

FIG. 1 illustrates various biochemical pathways mediated by latexin that may be involved in the regulation of HSC proliferation in mammals. Lxn is the only known endogenous carboxypeptidase A (CPA) inhibitor in mammals. Structural similarity between latexin and cystatins that inhibit cathepsins in the lysosomal protein degradation pathway suggests an inflammatory role of latexin in activated macrophages. Thus, latexin may be involved in the metabolism of specific proteins that are essential for HSC functions. Lxn appears to exhibit two potential Ca2+/calmodulin-dependent protein kinase sites and one c-GMP-dependent protein kinase phosphorylation site. Thus, the c-GMP/PKG and/or calcium/calmodulin signaling pathways may be involved in the Lxn-mediated regulation of HSCs. The physical structure of latexin includes two nearly identical domains that have high conformational homology with the cystatins that can inhibit cathepsins in the lysosomal protein degradation pathway. Thus, Lxn appears to have an inflammatory role in activated macrophages, and to be involved in the metabolism of specific proteins that are essential for HSC functions. The c-GMP/PKG and/or calcium/calmodulin signaling pathways may be involved in Lxn-mediated regulation of HSCs based on the fact that Lxn contains two potential Ca2+/calmodulin dependent protein kinase sites and one c-GMP-dependent protein kinase phosphorylation site. These possible pathways may act synergistically or independently in the regulation of HSC cycling, apoptosis, and/or proliferation that affect HSC population size.

The mechanism for transcriptional regulation of latexin appears to be related to the unique molecular architecture of the Lxn gene locus, that includes multiple SNPs within potential regulatory regions. The Lxn gene locus is located within an intron of Gfm1, a gene that encodes a translational elongation factor in mitochondria. Because Gfm1 was not differentially expressed amongst the congenic and background strains investigated, the differential transcriptional regulation of the embedded Lxn was unique. The specific promoter and/or enhancer regions of Lxn appear to be highly gene-specific and to enable differential gene regulation. A potential mechanism for differential gene expression between B6 and D2 alleles is suggested by the identification of clusters of confirmed SNPs sites within the potential promoter region of Lxn that are spatially concordant with two putative binding sites for transcription factors known to regulate stem cells. For example, a cluster of SNPs (SNPs 1-3) in the canonical Lxn promoter region is consistent with a region identified by ESPEER as potentially possessing regulatory activity. The SNP2 is located in the middle of the canonical core binding site in one of two adjacent potential binding sites for the transcription factor CBF1. The CBF1 is associated with the Notch-signaling pathway, known to be play a role in the regulation of stem cell population size. The SNPs 10 and 11 are in close proximity, or reside within potential regulatory regions, identified by ESPERR and TraFaC. The HNF1/TCF1, a transcription factor with two adjacent binding sites close to SNP11, can mediate events downstream of the canonical Wnt/beta-catenin-signaling pathway known to be involved in HSC regulation and to interact with the Notch-signaling pathway.

III. Methods for Inhibiting Latexin Expression and/or Latexin Activity

A. Ex Vivo Methods

Various embodiments provide ex vivo methods for producing a renewed population of hematopoietic stem cells (HSCs) in which the method comprises obtaining a first HSC population from a donor, contacting the first HSC population with an antagonist that reduces latexin expression and/or latexin activity, and culturing the HSC population under in vitro conditions that promote cell proliferation and/or inhibit apoptosis to obtain a second HSC population that comprises a progeny of the first HSC population.

The first HSC population and the second HSC population can express any of the following combination of cell surface markers characteristic of HSCs: Thy-1$^{lo}$ Sca-1$^+$ Lineage$^-$ c-kit$^+$; or CD150$^+$ CD48$^-$ Sca-1$^+$ Lineage$^-$ c-kit$^+$; or Thy-1$^{lo}$ CD150$^+$ CD48$^-$ Sca-1$^+$ Lineage$^-$ c-kit$^+$.

The first HSC population can be obtained from a biopsy removed from a donor employing techniques known by persons skilled in the art, including the removal of stem cells from the bone marrow of a donor from large bone masses utilizing a large needle intended for bone marrow harvesting. The amount of hematopoietic stem cells needed as the first HSC population for the present method is less than the amount of hematopoietic stem cells needed for a conventional bone marrow transplantation that may require hundreds of needle insertions to obtain sufficient material for direct transplantation into a recipient host. Alternatively, HSCs may be collected by apheresis, a process in which a donor's peripheral blood is withdrawn through a sterile needle and passed through a device that removes white blood cells, and that returns the red blood cells to the donor. The peripheral stem cell yield can be increased with daily subcutaneous injections of granulocyte-colony stimulating factor. The HSCs are preferably obtained from human donors, however, non-human donors are also contemplated, including non-human primates, pigs, cows, horses, cats, and dogs. A purified population of HSCs may be obtained by utilizing various methods known by persons skilled in the art and described in U.S. Pat. No. 5,677,136; and U.S. Patent Publication No. 2006/0040389, which are incorporated by reference in their entirety.

Suitable antagonists include SiRNAs, ribozymes, antisense oligodeoxynucleotides, and small molecule compounds that can reduce latexin expression and/or latexin activity. Examples of suitable antagonists and methods for producing or identifying such antagonists are described below in Subsection C. A therapeutically effective latexin antagonist can promote HSC proliferation and/or suppress apoptosis by at least 25%. Suitable antagonists are further defined above in Subsection I.

Contacting the first HSC population with an antagonist that reduces latexin expression and/or latexin activity can promote cell proliferation and/or inhibit apoptosis provided that the first HSC population is cultured under suitable in vitro conditions. Latexin expression and/or latexin activity include intracellular processes that regulate latexin promoter activation, transcriptional activation, transcriptional termination, post-transcriptional processing, translational initiation, translational elongation, translational termination, and post-translational modification. Examples of suitable in vitro conditions are provided in U.S. Patent Publication No. 2005/0214262; U.S. Patent Publication No. 2006/0030041; and U.S. Patent Publication No. 2006/0030041, which are incorporated by reference in their entirety.

Latexin isoforms/variants suitable for antagonist-mediated targeting are provided above in Subsection I.

In another embodiment, a HSC population produced by the present methods is disclosed, in which the HSCs comprise any of the following combination of cell surface markers characteristic of HSCs: Thy-1$^{lo}$ Sca-1$^+$ Lineage$^-$ c-kit$^+$; or CD150$^+$ CD48$^-$ Sca-1$^+$ Lineage$^-$ c-kit$^+$; or Thy-1$^{lo}$ CD150$^+$ CD48$^-$ Sca-1$^+$ Lineage$^-$ c-kit$^+$.

Various embodiments provide methods for reconstituting a recipient host with a population of hematopoietic stem cells (HSCs) generated ex vivo, in which the method comprises obtaining a first HSC population from a donor, contacting the first HSC population with an antagonist that reduces latexin expression and/or latexin activity, culturing the HSC population under in vitro conditions that promote cell proliferation and/or inhibit apoptosis to obtain a second HSC population comprising a progeny of the first HSC population, and providing the second HSC population to the recipient host in need of HSC reconstitution.

The present methods are useful for the treatment of a recipient host affected with a disease of the blood, a disease of the bone marrow, a cancer of the blood, and a cancer of the bone marrow, an immunological disorder, anemia, leukemia, thalassemia major, sickle-cell disease, myelodysplastic syndrome, lymphoma, aplastic anemia, and/or multiple myeloma. Disorders suitable for treatment by the present methods include disorders that reduce the number of endogenous HSC population, such as genetic disorders that result in sub-optimal number of HSCs, cancers that result in sub-optimal number of HSCs, post-irradiation conditions that result in sub-optimal number of HSCs, and post-chemotherapy conditions that result in sub-optimal number of HSCs.

The HSC population generated ex vivo by the present methods are transferred into a recipient host in need of HSC reconstitution. Such HSC populations that have been exposed to the antagonist, and that have been expanded can be infused intravenously into the blood stream of the recipient host. The antagonist-exposed and pre-expanded HSC population can localize within local niches of a bone marrow after a brief circulation in the blood stream. The antagonist-induced and pre-expanded HSC population may be able to respond to various growth factors produced by endothelial cells within the local bone marrow niches that may contribute to further proliferation and/or suppression of apoptosis of the antagonist-exposed and pre-expanded HSC population. Reconstitution of HSCs within the recipient host is achieved when the total number of HSCs within the recipient host is at least 25% greater than before transplantation of the antagonist-induced and pre-expanded HSC population.

In one embodiment, the donor is the same organism as the recipient host in that the donor has identical HLA haplotype as the recipient host, and wherein the recipient host is reconstituted with autologous HSCs when provided with the second HSC population. For example, allogenic bone marrow transplantation involves two persons, a (non-diseased) donor and a (diseased) patient-recipient. In autologous transplantation, the risks for developing graft rejection, infection, and Graft Verses Host Disease ("GVHD") are reduced.

In another embodiment, the donor is not the same organism as the recipient host, and the donor has a HLA haplotype of sufficient similarity to the HLA haplotype of the recipient host, and wherein the recipient host is reconstituted with allogenic HSCs when provided with the second HSC population. For optimal results, the allogeneic HSC donors should have identical human leukocyte antigens ("HLA") as the recipient host, and the recipient host should receive immunosuppressive medications. For example, an allogenic transplant donor may be a relative (e.g., a sibling) or an unrelated volunteer.

B. In Vivo Methods

Various embodiments provide methods for reconstituting a recipient host with a population of hematopoietic stem cells (HSCs) generated in vivo in which the method comprises administering to the recipient host a pharmaceutical composition comprising an antagonist that reduces latexin expression and/or latexin activity.

The present methods enable clinicians to promote HSC proliferation within the bone marrow of patients affected by any type of disorder, disease, or cancer that may reduce the supply of endogenous HSCs to less than an optimal number. The recipient host is affected with a disease of the blood, a disease of the bone marrow, a cancer of the blood, and a cancer of the bone marrow, an immunological disorder, anemia, leukemia, thalassemia major, sickle-cell disease, myelodysplastic syndrome, lymphoma, aplastic anemia, and/or multiple myeloma.

The pharmaceutical composition comprises a therapeutically effective amount of the antagonist. The pharmaceutical composition further comprises a pharmaceutical excipient known by persons skilled in the art. Pharmaceutical formulations for effective delivery of pharmaceutical composition will vary depending on the latexin antagonist and mode of administration. Suitable pharmaceutical carriers are known by persons skilled in the art (Remington's Pharmaceutical Sciences (1989), which is incorporated in entirety). Pharmaceutical compositions can be administered by various methods, including by injection, oral administration, inhalation, transdermal application, or rectal administration. For oral administration, suitable formulations containing a pharmaceutical compound and pharmaceutically-compatible carriers can be delivered in various forms, such as tablets or capsules, liquid solutions, suspensions, emulsions, and the like. For inhalation, suitable formulations containing a pharmaceutical compound and pharmaceutically-compatible carriers can be delivered as aerosol formulations that can be placed into pressurized propellants, such as dichlorodifluoromethane, propane, nitrogen, and the like. For parenteral administration, suitable formulations containing a pharmaceutical compound and pharmaceutically-compatible carriers can be delivered by intra-articular, intra-venous, intra-muscular, intra-dermal, intra-peritoneal, and sub-cutaneous routes.

Pharmaceutical compositions suitable for use include compositions containing active ingredients in an effective amount to achieve its intended purpose. More specifically, a therapeutically-effective amount means an amount effective to promote the proliferation of HSCs and/or inhibit apoptosis of HSCs in subjects exposed to the present pharmaceutical compositions. Determination of the effective amounts is well within the capability of persons skilled in the art. A dose can be formulated in animal models to achieve a circulating concentration range that includes IC50 value, defined as a dose in which 50% of cells of a culture show an effect due to the test compound. Such information can be used to more accurately determine useful doses in human subjects.

Toxicity and therapeutic efficacy of such compounds can be determined by standard pharmaceutical procedures utilizing cell cultures or experimental animals in order to determine a LD50 value, the dose determined to be lethal to 50% of the exposed population, and to determine a ED50 value, the dose determined to be therapeutically effective in 50% of the exposed population. A dose ratio between toxic effect and therapeutic effect is referred to as the "therapeutic index," or it can be expressed as the ratio of the LD50 value over the ED50 value. Compounds that exhibit high therapeutic indices are preferred. The data obtained from cell culture assays and animal studies can be used in formulating a range of effective dosage for human usage. Optimal dosage range includes a ED50 dose with minimal toxicity, although the dosage may vary within this range depending on a given pharmaceutical formulation and route of administration. Dosage administered to a subject should be adjusted according to the age of the subject, the weight of the subject, the manner of administration, and other circumstances unique to each subject.

C. Exemplary Antagonists that Inhibit the Expression and/or Activity of Latexin and Latexin Isoforms/Variants A HSC population obtained from a donor can be induced to proliferate ex vivo under in vitro conditions, or an endogenous HSC population within a patient can be induced to proliferate in situ by exposing the HSC population of interest to various antagonists that can inhibit latexin gene expression and/or latexin activity.

Suitable compositions that can inhibit the expression and/or the activity of latexin and latexin variants include sequence-specific polynucleotides that can interfere with the transcription of endogenous latexin gene; sequence-specific polynucleotides that can interfere with the translation of latexin mRNA transcripts (e.g., siRNAs, ribozymes); sequence-specific polypeptides that can interfere with the protein stability of latexin, the enzymatic activity of latexin, and/or the binding activity of latexin with respect to substrates and/or regulatory proteins; antibodies that exhibit specificity for latexin; and small molecule compounds that can interfere with the protein stability of latexin, the enzymatic activity of latexin, and/or the binding activity of latexin. An effective antagonist can promote HSC proliferation by at least 25%, 30%; 35%, 40%, 45%, 50%, 55%, 60%, 65%, 70%, 75%, 80%, 85%, 90%, 95%, or 100%.

1. Sequence-Specific Compounds
a. RNAi Compounds

In one embodiment, various siRNAs that are complementary to human latexin mRNA and mammalian orthologs can be employed by persons skilled in the art to promote HSC proliferation and/or inhibit HSC apoptosis. By introducing such RNAi compounds to a recipient patient deficient in HSCs, the silencing or inactivation effect of RNAi compounds on latexin gene/gene products within the HSCs can promote HSC proliferation and/or inhibit HSC apoptosis. Because introduction of double-stranded RNA ("dsRNA") that are longer than 30 nucleotides into mammalian cells induces a sequence-nonspecific interferon response, alternative methods for delivery of interfering RNA molecules ("RNAi") may be suitable. For example, most common form of RNAi molecules are short-interfering RNAs ("siRNAs") of 21-23 base-pairs that are chemically or enzymatically synthesized, which can be introduced into mammalian host cells by various methods, including transfections. However, unlike fungi, plants, and worms that can replicate siRNAs in vivo, transfection of siRNA produces only transient gene-silencing effect in mammalian cells. As an alternative, DNA vectors encoding precursor-like forms of siRNAs may be used for stable production of siRNAs in vivo in various hosts, including mammalian cells.

In another embodiment, compounds that can promote HSC proliferation and/or inhibit HSC apoptosis are contemplated, in which the compounds comprise an oligonucleotide that can interact with endogenous messenger RNA encoded by latexin gene or by latexin isoforms having at least about 70%, 75%, 80%, 85%, 90%, 95%, 96%, 97%, 98%, or 99% sequence similarity to SEQ ID NO:1 (i.e., a sense-strand of human latexin cDNA). Such RNA oligonucleotide compounds can be single-stranded or double-stranded. Suitable lengths of RNA oligonucleotides include molecules containing 15-20 nucleotides, 20-30 nucleotides, 30-50 nucleotides, 50-75 nucleotides, 75-100 nucleotides, 100-150 nucleotides, 150-200 nucleotides, and 200-300 nucleotides. In another embodiment, the present invention is directed to compounds that can promote HSC proliferation and/or inhibit HSC apoptosis, the compounds include an anti-sense strand that can hybridize to an endogenously produced messenger RNA, and that can inhibit the translation of the messenger RNA.

Selection of efficient siRNAs is an empirical process, but certain rules governing optimal selection of siRNAs are known. The sequence selected for a siRNA appears to be critical. For example, siRNAs containing sequence motifs, such as $AAN_{19}TT$, $NAN_{19}NN$, $NARN_{17}YNN$, and $NANN_{17}YNN$, are effective, in which N is any nucleotide, R is a purine, and Y is a pyrimidine. In addition, regions of complementary DNA should have non-repetitive sequences, and should avoid intronic sequences. Suitable siRNAs contain approximately 30-70% GC content, contain even representation of all nucleotides on the anti-sense strand, and do not contain stretches of single nucleotide, especially stretches of Gs. Designing suitable SiRNA molecules is within the scope of persons skilled in the art. The following references are herein incorporated by reference in their entirety: Henschel et. al., Nucleic Acids Research, Vol. 32: 113-120 (2004); Naito et al., Nucleic Acids Research, Vol. 32: 124-129 (2004); Dorsett et al., Vol. 3: 318-329 (2004); and Brummelkamp et al., Nature Reviews, Vol. 3: 781-789 (2003); Pusch et al., Nucleic Acid Research, 31: 6444-6449 (2003); and Chiu et al., RNA 9: 1034-1048 (2003).

Although any region of mRNA can be theoretically targeted, certain sequences that are known binding sites for mRNA-binding proteins should be avoided, including untranslated regions, such as the "5'UTR" and "3'UTR," start-codons, and exon-exon boundaries. For some mRNA targets, siRNA-directed silencing may be more effective if the siRNA sequence is selected at least 50-100 nucleotides downstream of a start codon, and preferably directed towards the 3'end of a target mRNA. In addition, the conformation of a mRNA recognition site within an mRNA target is preferably RNAse-H-sensitive, and preferably not within a highly-structured RNA region. These guidelines are generally applicable since the choice of a siRNA depends on the target mRNA sequence, and persons skilled in the art would need to synthesize several siRNAs to validate the efficiency of each. The specificity of a siRNA for a single gene can be ascertained by performing a multiple-genome-sequence alignment, such as a BLAST search of the selected sequence against sequence databases, including "Unigene" libraries associated with National Center for Biotechnology Information (NCBI). Potential off-target silencing by siRNA may be minimized by choosing a siRNA sequence with maximum sequence divergence from a list of genes with partial-sequence identity to the intended mRNA target. General principles for siRNA selection are taught by the following two review articles, which are incorporated by reference (Dorsett and Tuschl, Nature Reviews Vol. 3: 318-329, (2004); Dykxhoorn et al., Nature Reviews Vol. 4: 457-467 (2003)).

Various expression vectors can be constructed to enable stable production of siRNA-like molecules in vivo. For example, RNA-pol II promoters may be operably-linked to a hairpin precursor of a siRNA sequence of interest. RNA-pol II promoters represent a broad range of promoters that enable substantial control over parameters governing RNA expression, such as inducible, constitutive, tissue-specific, or developmentally-regulated RNA expression. Alternatively, RNA-pol III promoters may be used to produce short RNA species that do not activate the interferon pathway. Suitable RNA-pol III promoters include class III promoters that lack essential transcriptional elements downstream of a transcription initiation site, such as U6 and H1 promoters, which may be operably-linked to a siRNA-encoding sequence.

Long-hairpin RNAs, imperfect shRNAs, miRNAs, and siRNAs, can be designed as follows. For example, a sub-sequence of a messenger RNA encoded by latexin gene or by latexin isoforms having at least about 70%, 75%, 80%, 85%, 90%, 95%, 96%, 97%, 98%, or 99% sequence similarity to SEQ ID NO:1 (i.e., a sense-strand of human latexin cDNA), can be targeted. For example, an anti-sense strand of shRNA can be designed by selecting a sub-sequence portion of a RNA sequence complementary to endogenous latexin messenger RNA and latexin isoforms having at least about 70% sequence similarity to SEQ ID NO:1

For designing shRNA, the composition and size of the loop and length of the stem of a hairpin duplex should be considered. Suitable stem lengths for efficient silencing include a broad range, including stem lengths of 19-29 nucleotides. Suitable loop lengths for efficient silencing include a broad range, including loop lengths of 4-23 nucleotides. In certain context, hairpin structures with duplexed regions that are longer than 21 nucleotides may promote effective siRNA-directed silencing, regardless of loop sequence and length.

Various gene-delivery vectors that are practiced by persons skilled in the art can be used to introduce the present expression vectors. Examples of viral vectors that may be used to infect HSC cells include: improved adenoviral vectors (Reynold et al., Nature Biotechnology 19: 838-842 (2001)); gene-deleted adenovirus-transposon vectors (Yant et al., Nature Biotechnology 20: 999-1005 (2002)); recombinant adenoviruses (Bilang-Bleuel et al., Proc. Natl. Acad. Sci. U.S.A. 94:

8818-8823 (1997)); the Moloney-murine-leukemia-virus ("Mo-MuLV") based retroviral vectors (Auten et al., Human Gene Therapy 10: 1389-99 (2003)); and poliovirus-replicon-based vectors (Bledsoe et al., Nature Biotechnology 18: 964-969 (2000)). Examples of other suitable viral vectors include: herpes virus, mumps virus, Sindbis virus, vaccinia virus, such as the canary pox virus, and lentivirus. The usage of viral vectors is well known by persons skilled in the art, and for gene therapy uses, viral infection is preferred generally. The following references are incorporated by reference in their entirety: Robbins and Ghizzani, Mol. Med. Today 1:410-417 (1995); Robin et al., Stem Cells 20:514-521 (2002); Chen et al., Immunity 19:525-533 (2003); North et al., Immunity 16: 661-672 (2002); Zhou et al., Nature Medicine 7: 1028-1034 (2001); Ivanova et al., 298: 601-604 (2002); and Santos et. al., Science 298: 597-600 (2002).

b. Chemically Modified Anti-Sense Oligodeoxyribonucleic Acids ("ODNs")

In one embodiment, various oligodeoxyribonucleic acid (ODN) molecules that are complementary to endogenous messenger RNA encoded by latexin gene or by latexin isoforms having at least about 70%, 75%, 80%, 85%, 90%, 95%, 96%, 97%, 98%, or 99% sequence similarity to SEQ ID NO:1 (i.e., a sense-strand of human latexin cDNA), can be employed by persons skilled in the art to promote HSC proliferation and/or to inhibit HSC apoptosis. By introducing such oligodeoxyribonucleic acid (ODN) molecules to a recipient patient deficient in HSCs, the silencing or inactivation effect of RNAi compounds on latexin gene/gene products within the HSCs can promote HSC proliferation and/or inhibit HSC apoptosis. Suitable oligodeoxyribonucleic acid molecules ("ODNs") are short polynucleotides of approximately 20 nucleotides in length, that can hybridize with pre-mRNA and mRNA to form RNA-DNA duplexes, which are degraded by ribonuclease H ("RNase H"). Such ODNs can be chemically modified to prevent the action of RNase H, to inhibit translation of mRNA by steric hindrance, to inhibit splicing of pre-mRNAs, and to inhibit transcription by the formation of triple helices. Kurreck, J. et al., Eur. J. Biochem., 270:1628-1644 (2003); Baker et al., J. Biol. Chem., 272: 11994-2000 (1997); Lu, Q. L. et al, Nature Med., 9:1009-1014 (2003); and Uil, et al., Nucleic Acids Res., 31:6064-6078 (2003) are incorporated by reference in their entirety.

c. Ribozymes

In one embodiment, various ribozymes containing sequences that are complementary to endogenous messenger RNA encoded by latexin gene or by latexin isoforms having at least about 70%, 75%, 80%, 85%, 90%, 95%, 96%, 97%, 98%, or 99% sequence similarity to SEQ ID NO:1 (i.e., a sense-strand of human latexin cDNA), can be employed by persons skilled in the art in order to reduce latexin expression and/or latexin activity that results in HSC proliferation and/or HSC apoptosis. Ribozymes, including the "hammer-head" ribozyme, are RNA molecules that bind target mRNA by assuming a unique secondary structure when hybridized to target mRNA, which enables catalytic hydrolysis of a phosphodiester bond within in the backbone of target mRNA. Efficient cleavage by a ribozyme requires the presence of divalent ions, such as magnesium, and is also dependent on target RNA structure, and relative proximity between ribozyme and target molecule. RNA-localization signals or RNA chaperones may be used so that low concentrations of ribozymes are sufficiently effective in silencing latexin and latexin isoforms. Ribozymes can be chemically synthesized in vitro, and can be transcribed from expression vectors in vivo. Methods for ribozyme construction and utilization are known by persons skilled in the art. Doudna and Cech, Nature, 418:222-228 (2002); Kuwabara et al, J. Biochem., 132:149-155 (2002); Michienzi and Rossi, Methods Enzymol., 341:581-596 (2001); and Good et al., Gene Ther. 4:45-54, (1997) are herein incorporated by reference.

d. Other Compounds

In another embodiment, suitable antagonists include compounds that can interact with polypeptides having at least about 70%, 75%, 80%, 85%, 90%, 95%, 96%, 97%, 98%, or 99% sequence similarity to SEQ ID NO:2, that can inhibit the activity of the bound polypeptide, and that can promote the proliferation of HSCs and/or suppress the apoptosis of HSCs. In addition, compounds that can interact with genomic DNA containing exons having at least about 70%, 75%, 80%, 85%, 90%, 95%, 96%, 97%, 98%, or 99% sequence similarity to SEQ ID NO:1 (i.e., a sense-strand of human latexin cDNA) can be employed. In addition, compounds that can interact with RNA transcripts encoded by a gene, in which the exon sequences have at least about 70%, 75%, 80%, 85%, 90%, 95%, 96%, 97%, 98%, or 99% sequence similarity to SEQ ID NO:1 (i.e., a sense-strand of human latexin cDNA) can be employed. Various compounds that can inhibit the expression and/or activity of latexin or latexin isoforms can be either naturally-occurring or synthetically-produced. Large combinatorial libraries of chemical/biological compounds can be generated by various chemical and biological synthesis methods known in the art. Such combinatorial chemical libraries include: small organic molecule libraries (benzodiazepines, Baum C&EN, Jan. 18, page 33 (1993)); Chen et al., J. Amer. Chem. Soc. 116:2661 (1994)), such as isoprenoids (U.S. Pat. No. 5,569,588), thiazolidinones and metathiazanones (U.S. Pat. No. 5,549,974), pyrrolidines (U.S. Pat. Nos. 5,525,735 and 5,519,134), morpholino compounds (U.S. Pat. No. 5,506, 337), and benzodiazepines (U.S. Pat. No. 5,288,514), oligo-carbamates (Cho et al., Science 261:1303 (1993)), and peptidyl phosphonates (Campbell et al., J. Org. Chem. 59:658 (1994)). Exemplary combinatorial libraries include: various peptide libraries (U.S. Pat. No. 5,010,175; Furka, Int. J. Pept. Prot. Res. 37:487-493 (1991); Houghton et al., Nature 354: 84-88 (1991)); peptoid libraries (PCT Publication No. WO 91/19735); encoded peptides (PCT Publication No. WO 93/20242); random bio-oligomers (PCT Publication No. WO 92/00091); benzodiazepines (U.S. Pat. No. 5,288,514); diversomers such as hydantoins, benzodiazepines and dipeptides (Hobbs et al., Proc. Nat. Acad. Sci. USA 90:6909-6913 (1993)); vinylogous polypeptides (Hagihara et al., J. Amer. Chem. Soc. 114:6568 (1992)); nonpeptidal peptidomimetics with glucose scaffolding (Hirschmann et al., J. Amer. Chem. Soc. 114:9217-9218 (1992)); various nucleic-acid libraries; various peptide-nucleic acid libraries (U.S. Pat. No. 5,539, 083); various carbohydrate libraries (Liang et al., Science, 274:1520-1522 (1996); U.S. Pat. No. 5,593,853)); and various antibody libraries (Vaughn et al., Nature Biotechnology, 14(3):309-314 (1996)).

D. Identification of Functionally-Related Isoforms of Latexin

The present methods and compositions can be employed for targeting variants of latexin that have similar properties/activities within HSCs of many types of mammalian subjects. Functionally-related isoforms of latexin can be identified by searching various genomic databases and conducting multi-genome-wide sequence alignments in order to identify homologous sequences of interest. Related orthologous sequences can be identified by searching composite genomic databases. The breath of a database search is limited by the scope of representative model organisms for which sequence data is available.

Homology can be determined by various methods, including alignments of open-reading-frames ("ORFs") contained in private and/or public databases. Any suitable mathematical algorithm may be used to determine percent identities and percent similarities between any two sequences being compared. For example, nucleic acid and protein sequences of the present invention can be used as a "query sequence" to perform a search against sequences deposited within various public databases to identify other family members or evolutionarily-related sequences. Genomic sequences for various organisms are currently available, including fungi, such as the budding yeast, or *Saccharomyces cerevisiae*; invertebrates, such as *Caenorhabditis elegans* and *Drosophila melangaster*; and mammals, such as the mouse, rat, and human. Exemplary databases for identifying orthologs of interest include Genebank, Swiss Protein, EMBL, and National Center for Biotechnology Information ("NCBI"), and many others known in the art. These databases enable a user to set various parameters for a hypothetical search according to the user's preference, or to utilize default settings. Tables 1-3, provided below, lists the accession numbers and gene identification numbers for exemplary mammalian orthologs. Suitable latexin variant that may be targeted for suppression or inhibition include the carboxypeptidase inhibitor (CARIN) described in U.S. Pat. No. 5,998,373.

TABLE 1

Gene Bank Accession Number for Exemplary Mouse, Human, and Rat Latexin mRNA.

| Organism | Accession Number | Gene IDS |
|---|---|---|
| Mus musulus (Mouse) | NM-016753 | 31980631 |
| Rattus norvegicus (Rat) | NM-031655 | 14269567 |
| Homo Sapiens (human) | NM-020169 | 21359932 |

TABLE 2

Gene Bank Accession Number for Exemplary Mouse, Human, and Rat Latexin Protein.

| Organism | Accession Number | Gene IDS |
|---|---|---|
| Mus musulus (Mouse) | NP-058033 | 31980632 |
| Rattus norvegicus (Rat) | NP-113843 | 14269568 |
| Homo Sapiens (human) | NP-064554 | 21359933 |

TABLE 3

Mammalian Homologs for Latexin

| Organism | Accession Number | Gene IDS | Percentage Identity | Gene Information |
|---|---|---|---|---|
| Mus musulus (Mouse) | AK032170.1 | 26327996 | 99.91 | Mus musculus adult male olfactory brain cDNA, RIKEN full-length enriched library, clone: 6430407E02 product: Latexin, full insert sequence |
| Mus musulus (Mouse) | AK149981.1 | 74211713 | 100.00 | Mus musculus bone marrow macrophage cDNA, RIKEN full-length enriched library, clone: G530111O19 product: Latexin,full insert sequence |
| Mus musulus (Mouse) | D88769.1 | 1669620 | 99.50 | Mus musculus mRNA for Latexin, complete cds |
| Mus musulus (Mouse) | AC124190.4 | 23499687 | 100.00 | Mus musculus BAC clone RP23-267M9 |
| Mus musulus (Mouse) | AC124190.4 | 23499687 | 100.00 | from 3, complete sequence |
| Mus musulus (Mouse) | AC124190.4 | 23499687 | 100.00 | |
| Mus musulus (Mouse) | AC124190.4 | 23499687 | 100.00 | |
| Mus musulus (Mouse) | AC124190.4 | 23499687 | 100.00 | |
| Mus musulus (Mouse) | AC124190.4 | 23499687 | 100.00 | |
| Mus musulus (Mouse) | AK018305.1 | 12857946 | 99.58 | Mus musculus 10 days neonate cerebellum cDNA, RIKEN full-length enriched library, clone: 6530401A10 product: Latexin, full insert sequence |

TABLE 3-continued

Mammalian Homologs for Latexin

| Organism | Accession Number | Gene IDS | Percentage Identity | Gene Information |
| --- | --- | --- | --- | --- |
| Mus musulus (Mouse) | AK198791.1 | 56022968 | 100.00 | Mus musculus cDNA, clone: Y1G0129D08, strand: minus, reference: ENSEMBL: Mouse-Transcript-ENST: ENSMUST0000 0058981, based on BLAT search |
| Mus musulus (Mouse) | AK187030.1 | 56011207 | 99.52 | Mus musculus cDNA, clone: Y0G0139J09, strand: minus, reference: ENSEMBL: Mouse-Transcript-ENST: ENSMUST0000 0058981, based on BLAT search |
| Rattus norvegicus (Rat) | Y18435.2 | 6066618 | 94.33 | Rattus norvegicus Latexin gene, exons 1 to 6 |
| Rattus norvegicus (Rat) | Y18435.2 | 6066618 | 96.92 | |

EXAMPLES

The following examples are offered by way of illustration and not by way of limitation. Examples 1 provides a map of congenic intervals defined in the reciprocal strains. Example 2 provides an in vitro method for determining HSC frequencies by cobblestone area-forming cell (CAFC) assay. Example 3 provides an in vivo method for determining HSC frequencies by a competitive limiting-dilution assay. Example 4 provides the identification of latexin by a genome-wide linkage analysis that correlates three QTL with HSC population size. Example 5 provides data that validates the linkage analysis and heritability of latexin. Example 6 provides the effect of latexin on HSC Replication. Example 7 provides the effect of latexin on HSC Self-renewal. Example 8 provides the effect of latexin expression on apoptosis. Example 9 provides microarray analysis of LSK cells. Example 10 provides Lxn mRNA levels in hematopoietic cells. Example 11 provides Lxn expression in undifferentiated and differentiated hematopoietic cell populations. Example 12 provides Lxn protein levels in hematopoietic cells of congenic and background strain mice. Example 13 provides Cis-Regulation of Lxn expression. Example 14 provides a decrease in stem cell numbers by the overexpression of Lxn.

Example 1

Mapping Congenic Intervals Containing Latexin

Figure 2:
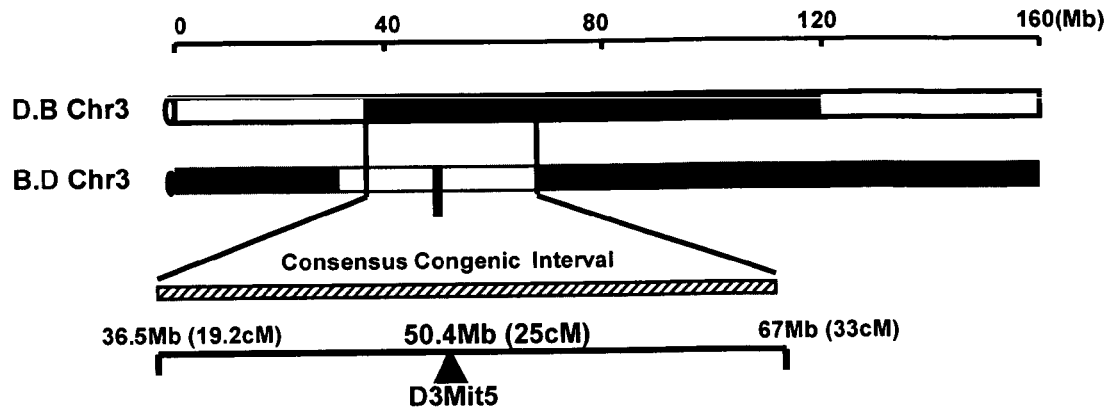
FIG. 2 illustrates a genomic map of congenic intervals identified in reciprocal Chr.3 congenic mouse strains, as described in Example 1.

FIG. 2 illustrates a genomic map of congenic intervals identified in reciprocal Chr.3 congenic mouse strains. The congenic interval, mutually inclusive in the two reciprocal strains, spans from 36.5 megabase (Mb) (19.2 centiMogan (cM)) to 67 Mb (33 cM), and the location of the marker (D3Mit5) most tightly linked to the trait is localized within 50.4 Mb (25 cM). The C57BL/6 ("B6") (Ptprc$^b$ [CD 45.2]) and DBA/2 ("D2") mice were background strains and purchased from the Jackson Laboratories (Bar Harbor, Me.). The total length of Chr3 (~160 Mb) is indicated on the top. Genomic interval with 95% of confidence limits of the linkage is indicated with the dashed bar. Data were analyzed by either student t-test by assuming unequal variance with $p<0.05$ (two-tail or one-tail as indicated), or by one-way ANOVA.

The Chr 3 congenic mice were generated by well-established methods known in the art. Mouse strains congenic for the Chr 3 QTL were generated by crossing the genomic interval harboring the QTL using D2, as the donor strain, and B6, as the recipient strain (symbolized as B.D Chr3), and vice versa (D.B Chr3). The two reciprocal congenic strains were derived by a 'speed congenic' approach involving at least eight backcrosses with the respective background strains. Both congenic lines were homozygous within their respective congenic intervals and genotyped exclusively for background strain alleles using 100 microsatellite markers scattered throughout the non-congenic genome. Congenic mice were genotyped every 6 months through genetic marker-based polymerase chain reaction. All primers for simple sequence repeat (SSR) element markers were bought from Research Genetics (Huntsville, Ala.). Two strains of Chr 3 congenic mice were generated and maintained: B.D Chr3 (14 cM~33 cM) congenics with D2 QTL being introgressed onto the B6 background, and their reciprocal congenic strains D.B Chr3 (19 cM~60 cM) with B6 QTL on a D2 background. B6.SJL (Ptprc$^b$ [CD 45.1]) mice from Charles River laboratories (Frederick, Md.) were used as transplantation recipients in competitive repopulation experiments. Female mice (6 to 10 weeks old) were housed in the animal facilities of the University of Kentucky under pathogen-free conditions according to NIH-mandated guidelines for animal welfare. They were fed with acidified water and food ad libitum.

Example 2

Determination of HSC Frequencies by In Vitro Cobblestone Area-Forming Cell (CAFC) Assay To quantify primitive hematopoietic cells derived from bone marrow in B6, D2, and 26 BXD RI strains, an in vitro cobblestone area-forming cell (CAFC) assay was performed. In this assay, each cobblestone area represents a population formed by clonal amplification of a single stem cell or a progenitor cell, and distinct populations arise in a chronological continuum. For determining the relative chronological age of a hematopoietic cell, the latency period is determined by measuring the duration before clonal expansion by a primitive hematopoietic cell. A longer latency period indicates a more primitive hematopoietic cell. Cobblestone areas were counted after 35 days of culture, a late time-point. Primitive hematopoietic cells measured at this time-point correlate strongly with long-term repopulating stem cells in vivo.

Figure 4A:
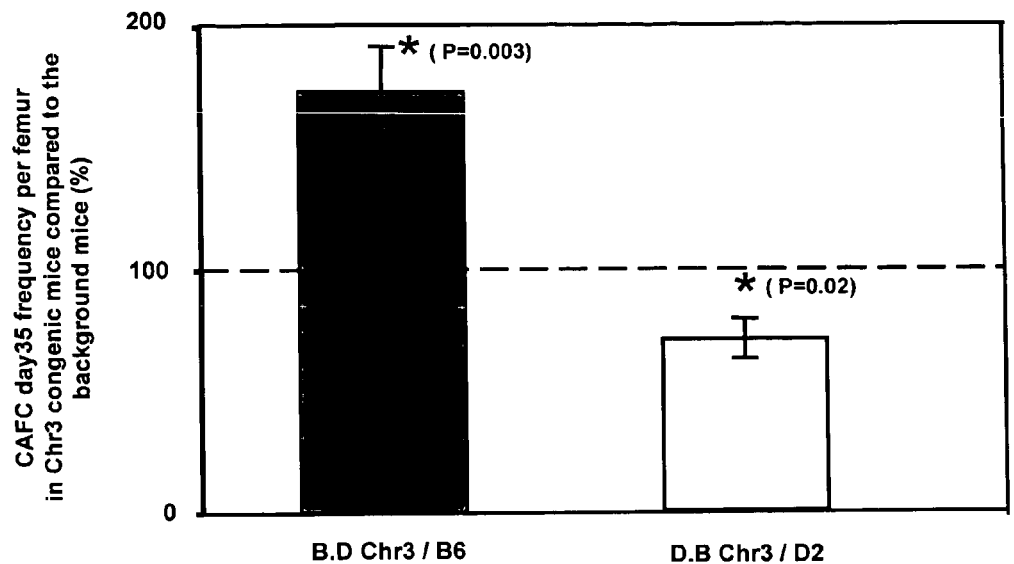
FIG. 4A illustrates the CAFC day 35 frequency observed for femur cells of Chr3 congenic mice compared to background mice, as described in Example 5.

Whole bone marrow cells and sorted LSK cells, described below in Example 5 and FIGS. 4A-4B, were evaluated in a cobblestone area-forming cell (CAFC) assay. In brief, a confluent monolayer of FBMD-1 stromal cells was established in 96-well tissue culture-treated plates (Costar, Cambridge, Mass.). After 7 to 10 days, wells were seeded either with unfractionated marrow at a dose of 81,000, 27,000, 9,000, 3,000, 1,000, or 333 cells per well, or with sorted LSK cells at a dose of 1, 3, 10, or 30 cells per well using an automated cell deposition unit. Twenty or 60 replicate wells per cell number were evaluated in experiments with unfractioned or sorted cells, respectively. The cells were cultured in Iscove's Modified Dulbecco Medium (IMDM), containing 20% horse serum, 80 U/mL penicillin, 80 mg/mL streptomycin (all from Life Technologies), $10^{-4}$ β-mercaptoethanol, and $10^{-5}$ M hydrocortisone (both Sigma, St. Louis, Mo.). Individual wells were screened at day 7, 14, 21, 28 and 35 for the presence of a cobblestone area, defined as a colony of at least 5 small, non-refractile cells growing underneath the stroma. A longer latency period before the appearance of cobblestones correlates with a more primitive state of the stem cell. Thus, the most primitive HSCs show cobblestones at day 35, whereas colonies that appear earlier are derived from more committed progenitor cells (HPCs). Frequencies of CAFCs were calculated by using maximum likelihood analysis and are equal to 1 divided by the number of cells yielding 37% negative wells. The frequencies of CAFC day 35 in BXD RI mouse strains were measured, and were used to perform genome-wide searches for linked loci within a GeneNetwork database.

Example 3

In Vivo Determination of HSC Frequencies in Rodents by Competitive Limiting-Dilution Assay A limiting-dilution analysis in competitively repopulated host animals was performed over a long term (20 week) period in order to functionally identify and to quantify HSCs in vivo. Graded numbers of bone marrow cells from B.D Chr3 congenic or B6 mice were first admixed with a fixed dose of competitor cells, and were transplanted into groups of lethally-irradiated mice. Lymphomyeloid reconstitution by either B.D Chr3 or B6-derived cells was assessed in the peripheral blood cells 20 weeks after transplantation. In limiting-dilution competitive repopulation assay, graded numbers (6,000; 20,000; and 60,000) of B.D Chr3 congenic or B6 "test" cells (CD45.2) were admixed with a radio-protective dose ($2 \times 10^5$) of competitor cells (CD45.1), and were injected intravenously into lethally irradiated (900 Gy) CD45.1 recipient mice.

Recipients were bled from the retro-orbital sinus 20 weeks after transplantation. Peripheral blood cell counts were performed on anesthetized mice bled from the retro-orbital venous plexus. Circulating leukocyte, erythrocyte, and platelet counts were measured by analysis of 40 ul blood using a System 9118+ Hematology Series Cell Counter (Biochem Immunosystems, Allentown, Pa.). Erthrocytes were depleted by hypotonic lysis using $NH_4Cl$. The leukocytes were stained in triplicate with fluorescein isothiocyanate (FITC)-conjugated anti-CD45.2 monoclonal antibody (mAb) (clone ALI4A2) and phycoerythrin (PE)-conjugated mAbs (Becton-Dickinson-PharMingen, San Diego, Calif.) specific for either B (anti-CD45R/B220; clone RA3-6B2) or T lymphocytes (anti-Thy-1.2; clone 30H12), or granulocytes (anti-Ly6G/Gr-1; clone RB6-8C5), and macrophages (anti-CD11b/Mac-1; clone M1/70). Samples were analyzed using a FACScan instrument (Becton-Dickinson Immunocytometry Systems, San Jose, Calif.). The frequencies of long-term HSCs were calculated from the proportions of negative recipients in each cell dose group by using L-Calc software (StemCell Technologies Inc., Vancouver, BC). In each cell dose group, <5% of the circulating B, T, and myeloid cells were regenerated from CD45.2 stem cells. The results obtained from two independent experiments showing the effect of D2 alleles on the number of long-term repopulating HSCs in B.D Chr3 mice are provided below in FIG. 4C in Example 5.

Example 4

Identification of Latexin by Linkage Analysis

Figure 3:
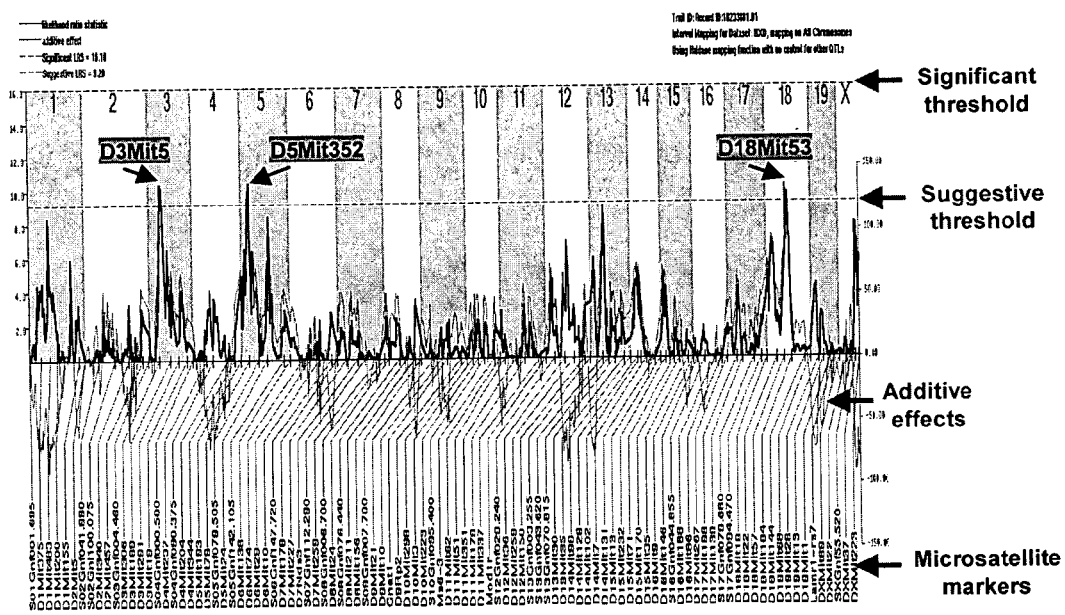
FIG. 3 illustrates a genome-wide linkage analysis based on GeneNetwork that associates the trait regulating HSC population size with three quantitative trait loci (QTL) on Chromosomes (Chr) 3, 5, and 18, respectively, as described in Example 4.

FIG. 3 illustrates a genome-wide linkage analysis based on GeneNetwork that associates the trait regulating HSC population size with three quantitative trait loci (QTL) on Chromosomes (Chr) 3, 5, and 18, respectively. In FIG. 3, these QTLs linked genetically to the trait of HSC population regulation at a 'suggestive' statistical level of association, in which the likelihood ratio statistic (LRS) values (solid blue line) for the corresponding markers (D3Mit5, D5Mit352, D18Mit53) are located between the suggestive threshold (dashed green line) and the significant threshold (dashed blue line). The 19 autosomes and Chr X of the mouse genome are labeled across the top, and some of microsatellite markers are listed across the bottom. The positive additive regression coefficient (solid red line) for each QTL indicates that D2 alleles increase the trait and that the B6 alleles decrease the trait. The positive additive regression coefficient for each QTL indicates that the D2 alleles have a positive effect on HSC population size and that the B6 alleles have a negative effect on HSC population size.

Example 5

Validation of the Linkage Analysis and Heritability of Latexin

To validate the results from genome-wide linkage analysis described in Example 4, CAFC day 35 assays were performed on whole bone marrow cells and LSK cells. FIG. 4A illustrates the CAFC day 35 frequency observed for femur cells (whole bone marrow cells derived from reciprocal congenic strains) of Chr3 congenic mice when compared to background mice. In FIG. 4A, introgression of D2 alleles onto the B6 background in the QTL region caused nearly a 2-fold increase in CAFC day 35 number (P=0.003) representing the number of HSCs in B.D Chr3 congenic mice, whereas the introgression of B6 alleles onto the D2 background caused more than a 50% decrease (P=0.02). The values are shown as mean± SEM (n>9). The absolute number of CAFC day 35 per femur (± SEM) for all strains as follows: B66: 397±59; B.D Chr3: 724±73; D2: 1978±684; D.B Chr3; 1532±286. Moreover, numbers for CAFC day 7 and day 21, which represent hematopoietic progenitor cells (HPCs) at different stages, and the cell counts for peripheral blood leukocytes, erythrocytes, and platelets showed no differences among congenic and background strains. This suggested that the Chr 3 QTL specifically regulates HSC population size.

Figure 4B:
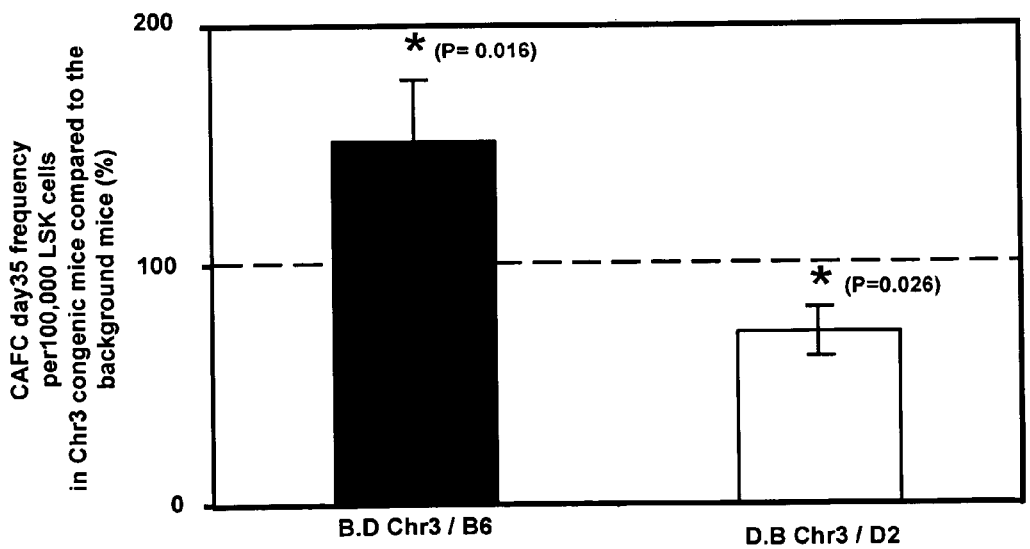
FIG. 4B illustrates the CAFC day 35 frequency observed for LSK cells of Chr3 congenic mice compared to background mice, as described in Example 5.

FIG. 4B illustrates the CAFC day 35 frequency observed for LSK cells of Chr3 congenic mice compared to background mice. The LSK cells represent a highly-enriched population of HSCs comprising about 0.03% of total marrow. In FIG. 4B, similar to results obtained with unfractionated marrow in FIG. 4A, the D2 alleles significantly increased the CAFC day 35 number when compared to B6 alleles exhibiting a decreased CAFC day 35 number in the LSK population (P<0.05). The values are shown as mean± SEM (n>9). The absolute number of CAFC day 35 per 100,000 Lin-negative, Sca-1+, c-kit+ cells (± SEM) for all strains as follows: B6: 1316±172; B.D Chr3: 2000±218; D2: 10000±1010; D.B Chr3; 7143±721. The LSK cells, were isolated by selecting a bone marrow population null for cell markers characteristic of lineage-specific differentiated blood cells (Lin-negative) and positive for the Sca-1 and c-Kit cell markers. This population was sorted using flow cytometry and assayed for CAFC day 35 numbers in 4 strains.

Figure 4C:
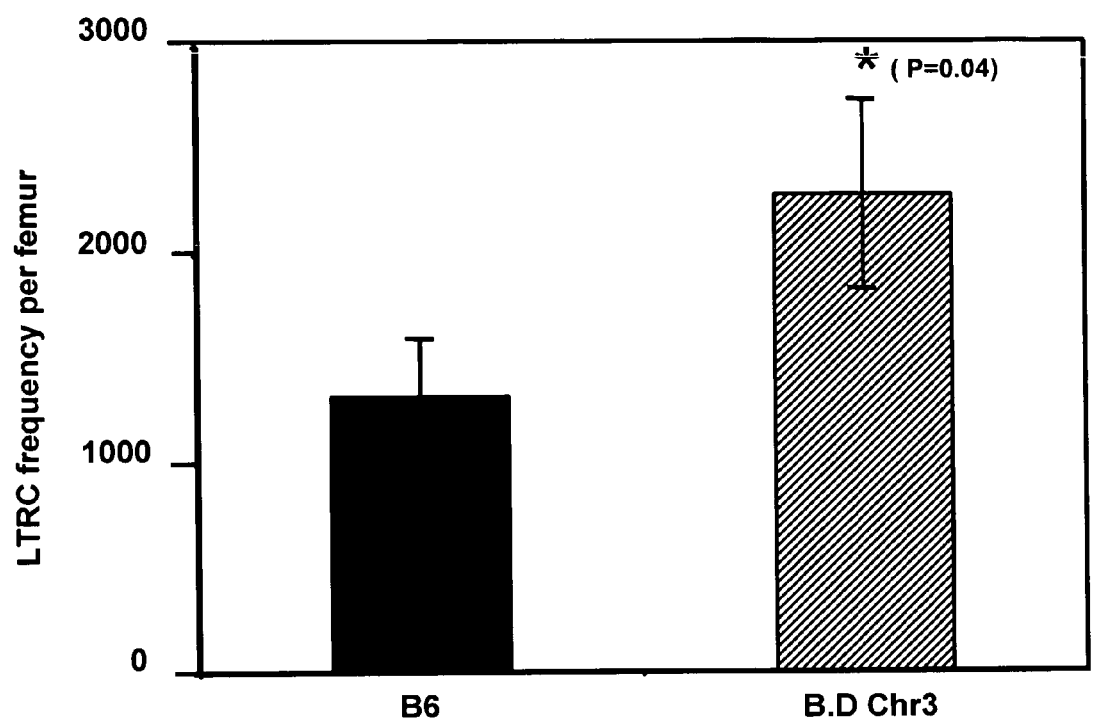
FIG. 4C illustrates the effect of D2 alleles on the number of long-term repopulating HSCs in B.D Chr3 mice, as described in Example 5.

FIG. 4C illustrates the effect of D2 alleles on the number of long-term repopulating HSCs in B.D Chr3 mice. In FIG. 4C, D2 alleles that introgressed in the region of the Chr 3 QTL caused a 73% increase in the total number of long-term repopulating HSCs (P=0.04) in B.D Chr3 mice compared to B6 mice, as determined from two independent experiments. Total number of long-term repopulating HSCs (LTRC) in B.D Chr3 congenic and B6 mice is shown, as average per femur (± SEM). LTRC frequencies were measured by competitive limiting-dilution analysis described below using femur cells of B6 and B.D Chr3 mice. Thus, both qualitatively and quantitatively, these results corroborated the results obtained in vitro.

A long-term, limiting-dilution analysis in competitively repopulated animal hosts was performed, as further described above in Example 3. Graded numbers of bone marrow cells from B.D Chr3 congenic or B6 mice were admixed with a fixed dose ($2 \times 10^5$) of competitor cells and transplanted into groups of lethally-irradiated mice irradiated to ablate their endogenous hematopoietic system. The competitor cells and recipient mice have a CD45.1 surface marker, whereas B.D Chr3 and B6 mice carry the CD45.2 marker on virtually all hematopoietic cells. This genetic marker is not presently available on the D2 background that also bears CD45.2, which precludes analogous experiments with the reciprocal congenic strain. Twenty weeks after transplantation, lympho-myeloid reconstitution by either B.D Chr3 or B6-derived cells was assessed in the peripheral blood cells 20 weeks after transplantation for the presence of CD45.2 cells by flow cytometry.

Together, these three independent studies support the conclusion that a Chr 3 QTL in the congenic intervals confers the phenotype (HSC population regulation), and confirms the results obtained by linkage analysis. In the context of these congenics, the QTL accounts for a significant portion of the natural variation of this parameter between the progenitor strains, despite 'suggestive' linkage of the phenotype with two other QTLs (Chr 5 and Chr18) and with the presence of several other QTLs that approach 'suggestive' linkage illustrated in FIG. 3.

Example 6

The Effect of Latexin Expression on HSC Replication

The effect of latexin expression on the proliferative activity of various primitive cells was assessed using two independent approaches. First, in vivo BrdU incorporation was used to determine cells in the S phase of the cell cycle. Mice were injected intraperitoneally with BrdU (1 mg per kg body weight) and sacrificed 90 minutes later. Bone marrow LSK cells were identified as described above. Analysis of BrdU incorporation in LSK was performed using BrdU Flow Kit (Pharmingen, San Diego, Calif.) according to the manufacturer's instruction. Second, the fraction of cells killed by a 1-hour in vitro incubation with hydroxyurea (HU) was measured. Hydroxyurea (HU) is an agent that blocks DNA synthesis and stops cell division by inhibiting ribonucleotide reductase. Briefly, all bone marrow cell suspensions were diluted to a concentration of $1 \times 10^7$ cells in 1 mL. Hydroxyurea (Sigma, St Louis, Mo.; 200 ug/mL, a total volume of 10 ul) was added to one sample, and incubated with the control sample for 1 hour at 33° C. The standard CAFC assay was then used to assay both HU-treated and control samples. The fraction of cells killed by HU was calculated by dividing the CAFC frequency in the HU-treated sample by the control value.

Figure 5A:
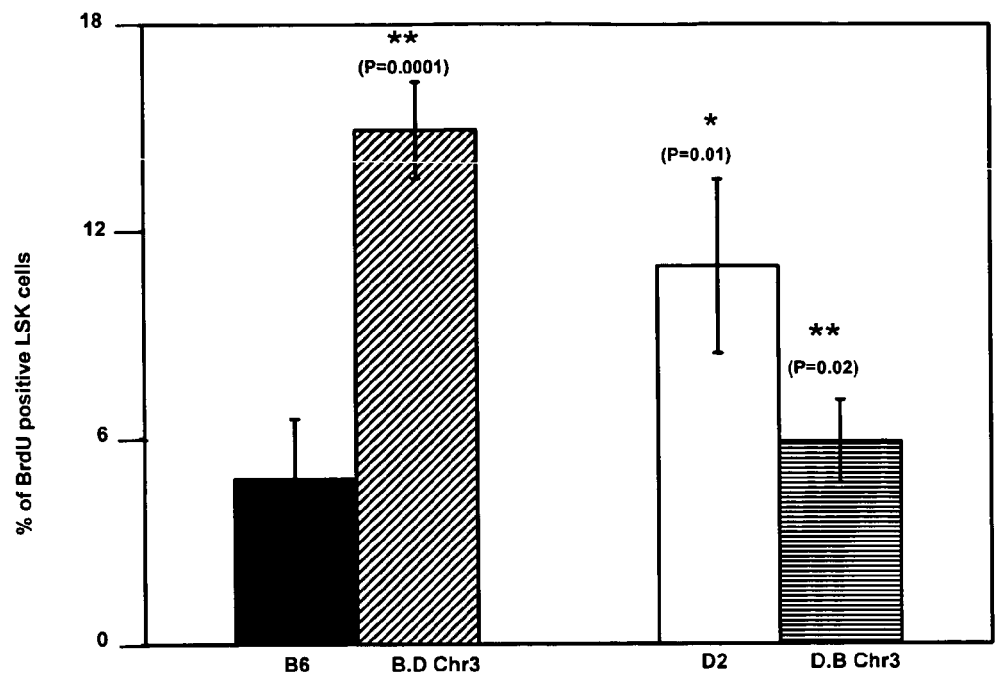
FIG. 5A illustrates that D2 alleles confer an increase in HSC replication and that B6 alleles confer a decrease in HSC replication, as described in Example 6.

FIG. 5A illustrates that D2 alleles confer an increase in HSC replication and that B6 alleles confer a decrease in HSC replication. The role of Chr 3 QTL in HSC replication, the proportion of LSK cells in S phase of the cell cycle were determined by measuring the incorporation of 5-bromodeoxyuridine (BrdU). In agreement with previous data, 4.5% (±1.7%) of B6 LSK cells were labeled with BrdU for one hour following administration in vivo, whereas more than twice as many D2 LSK cells were labeled under the same conditions (11%±2.5%) (P=0.01). In FIG. 5A, introgression of D2 alleles significantly increased the BrdU-positive LSK population (15%±1.4%) (P=0.0001) in B.D Chr3 congenic LSK cells, a proportion similar to that found in D2 cells. As expected, B6 alleles decreased the BrdU incorporation and conferred the B6 phenotype to D.B Chr3 cells (5.9%±1.2%). Replication of HSCs measured by BrdU incorporation in animals given a single pulse of BrdU. Results present the mean (±1 SD) of the fraction of BrdU positive LSK cells (n=8 per strain). * indicates the comparison between B6 and D2, and ** indicates the comparison between congenics and their respective background mice. P values are shown in the figure.

Figure 5B:
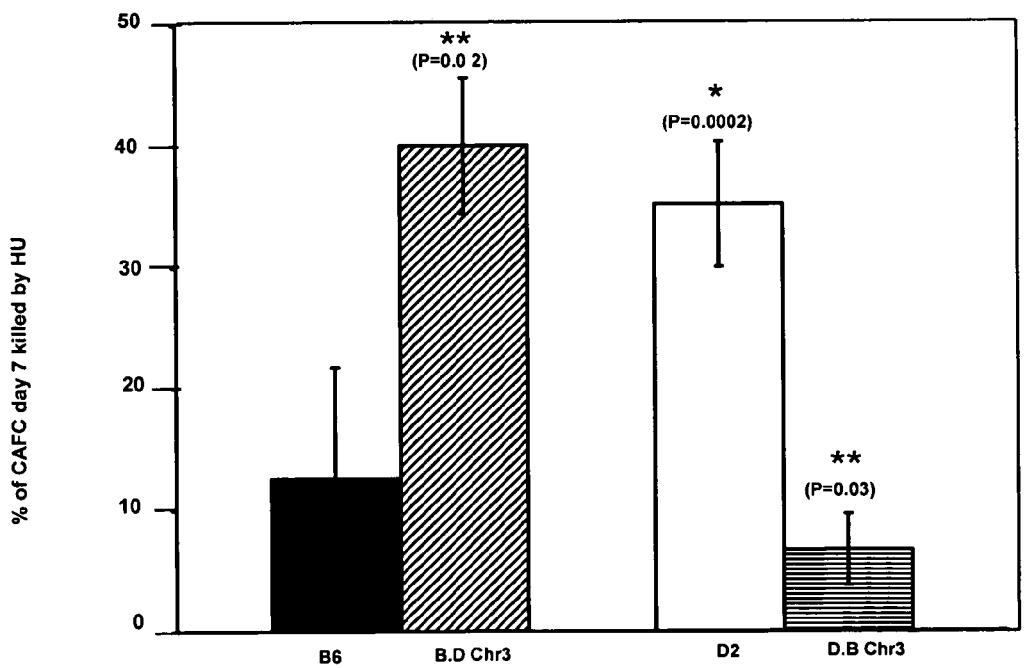
FIG. 5B illustrates the effect of Chr 3 QTL on the cell-cycle kinetics of hematopoietic progenitor cells (HPCs), as described in Example 6.

To determine the effect of QTL on cell cycle kinetics, the CAFC day 7 progenitor cells killed by hydroxyurea (HU) in the reciprocal congenic strains, B6, and D2 mice were measured. FIG. 5B illustrates the effect of Chr 3 QTL on the cell-cycle kinetics of the progeny of HSCs, also referred to as hematopoietic progenitor cells (HPCs). Proliferation of HPCs measured by CAFC day 7 cells killed by hydroxyurea (HU) in reciprocal congenic and B6, D2 strains. Data are shown as the average (±SD) of 3 independent experiments (n≧9). * indicates the comparison between B6 and D2, and ** indicates the comparison between congenics and their respective background mice. P values are shown in the figure. The results showed that the D2 alleles in and around the Chr 3 QTL in a B6 background quantitatively can reproduce the higher killing rate observed in D2 mice. Similarly, B6 alleles on a D2 background reproduced the entire variation in this trait between B6 and D2 mice. These results underscore the effect of the Chr 3 QTL on cell-cycle kinetics of HSC and their immediate progeny. Interestingly, progenitor cell numbers and differential blood cell counts showed no differences among the congenic and background strains, showing that compensatory mechanisms during downstream amplification of differentiating cells obviated the variation in the final cell outputs in the multiple blood cell lineages.

Example 7

The Effect of Latexin Expression on HSC Self-Renewal

The self-renewal capacity of B.D Chr3 congenic HSCs was tested in serial transplant experiments in which B.D Chr3 congenic HSCs and B6 marrow cells were co-transferred to recipients so that both types of cells competed for engraftment. In serial bone marrow transplantation, B.D Chr3 congenic or B6 "test" cells were injected into the primary recipients along with equal number of competitor cells ($1\times10^6$). Sixteen weeks after transplant, marrows were harvested from the primary recipients, and were transplanted into secondary recipients. An identical regimen was repeated twice more, culminating in engrafted quaternary hosts. At each transplant, the peripheral blood, bone marrow, and bone marrow LSK cells were analyzed. The competitive advantage and self-renewal capacities were analyzed by comparing the percentage of B.D Chr3 congenic-derived or B6-derived cells at each round of transplantation.

Figure 5C:
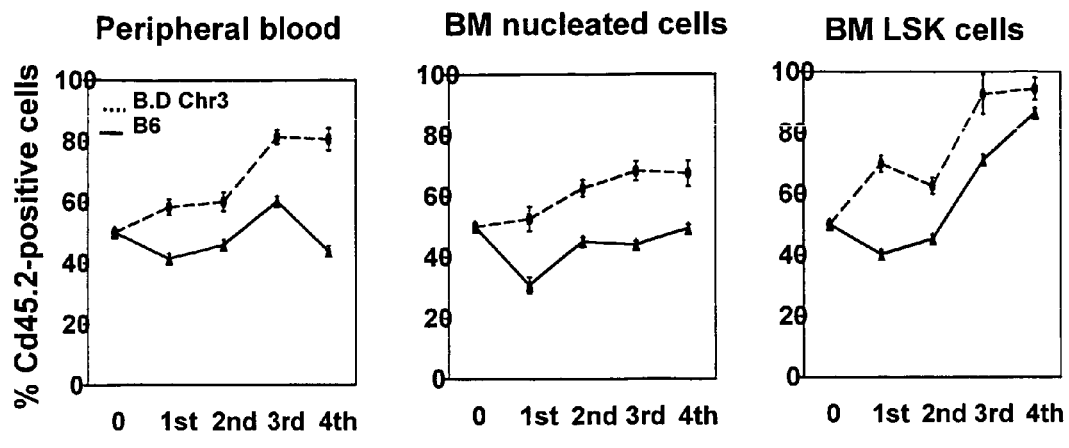
FIG. 5C illustrates that D2 alleles of the Chr 3 QTL confer HSCs with higher self-renewal capability, as described in Example 7.
Figure 5C:
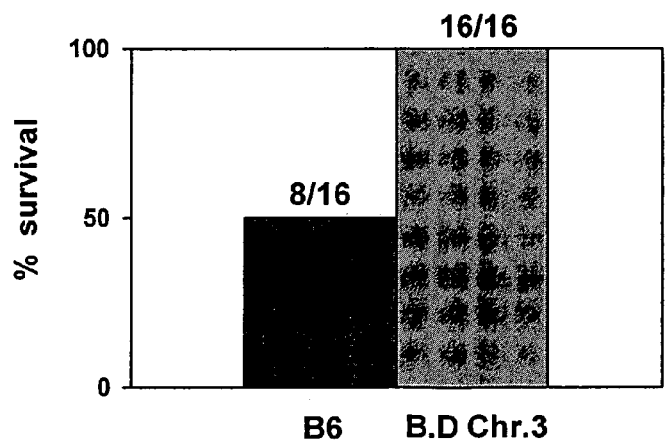

FIG. 5C illustrates that D2 alleles of the Chr 3 QTL confer HSCs with higher self-renewal capability. In FIG. 5C, congenic stem cells maintained their competitive advantage at every round of transplantation in each cell population, demonstrating that they retained the characteristic ability of stem cells to self-renew and to give rise to normal differentiated progeny when challenged with replicative stress. Consistent with the extensive self-renewal ability of B.D Chr3 stem cells, all (16) of the quaternary recipients transplanted with congenic cells survived long-term, whereas half (8 of 16) of the recipients receiving only B6 cells failed to survive to the 10-week evaluation time-point in $4^{th}$ generation recipients. Thus, serial bone marrow transplantation in a competitive repopulation setting clearly demonstrates that D2 Chr 3 QTL confers HSCs with higher self-renewal capability, and that this capacity is intrinsic to the HSCs. B.D Chr3 (dashed line) or B6-derived (solid line) peripheral blood leukocytes, BM nucleated and BM LSK cells were analyzed 16 weeks after they were transplanted into primary (1st), secondary (2nd), tertiary (3rd) and quaternary (4th) recipients. Each data point represents the average for groups of mice ($n \geq 16$). The survival rate of quaternary recipients transplanted with either B.D Chr3 or B6 cells is shown in the last panel.

Example 8

The Effect of Latexin Expression on Apoptosis

To determine whether allelic differences in the Chr 3 congenic interval affected steady-state apoptosis in HSC population, apoptosis was assessed by Annexin V-staining of bone marrow LSK cells.

Figure 5D:
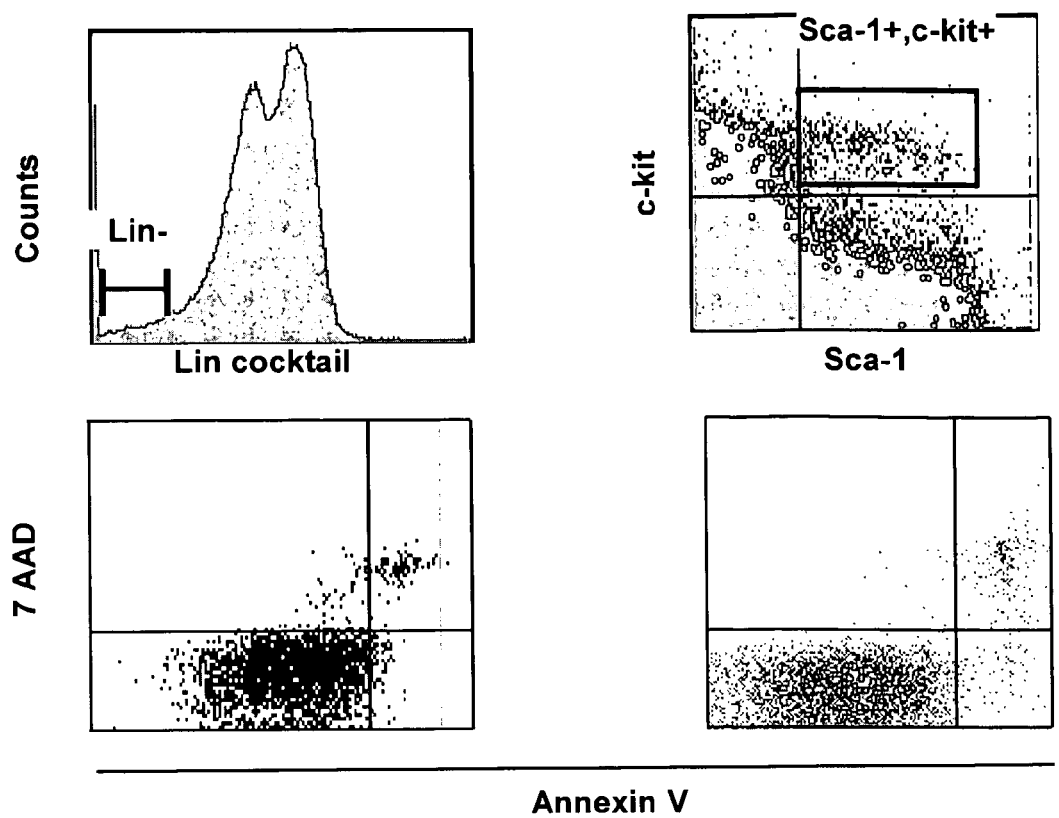
FIG. 5D illustrates bone marrow LSK cells subject to apoptosis as detected by Annexin V-staining, as described in Example 8.

FIG. 5D illustrates bone marrow LSK cells subject to apoptosis as detected by Annexin V-staining. Top two plots show the gates to identify Lin-negative, Sca-1+ and c-kit+ (LSK) stem cells. Bottom left plots identify Annexin V+, 7AAD-negative apoptotic cells in LSK cells. The plots on the right are from the thymocyte control for determination of Annexin V and 7AAD quadrants. Plots are from one representative animal.

Figure 5E:
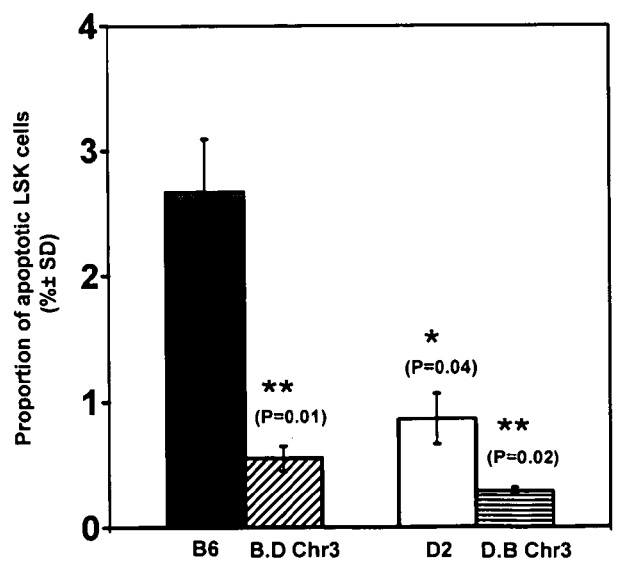
FIG. 5E illustrates the effect of Chr 3QTL on apoptosis of LSK cells in steady-state B6 D2 and Chr3 congenic bone marrows, as described in Example 8.

FIG. 5E illustrates Annexin V-stained LSK populations representing steady-state B6 and D2 bone marrow. In FIG. 5E, a significant variation ($P=0.04$) in Annexin V-staining in LSK populations representing steady-state B6 (2.7%±0.4%) and D2 (0.9%±0.2%) bone marrow was observed. The values for each strain are the mean (±1 SD) for 8 animals. * indicates the comparison between B6 and D2, and ** indicates the comparison between congenics and their respective background mice. P values are shown in the figure.

Introgression of D2 alleles around the Chr 3 QTL, in the B.D Chr3 congenic, resulted in an apoptotic LSK subpopulation (0.6%±0.1%) similar to that of D2 mice, which suggests that the congenic interval conferred the entire phenotype. Surprisingly, analysis of marrow from the reciprocal congenic strain revealed a very low (0.3%±0.03%) apoptotic LSK population. Thus, B6 alleles at and around the QTL do not confer the B6 phenotype onto D2 HSCs. In fact, apoptosis was significantly ($P=0.02$) less than in the D2 background strain. This result may be due to genes in the mutually exclusive congenic intervals of the reciprocal strains, or genes in the D2 background having a strong negative effect on HSC apoptosis. The results suggest that the QTL might act through a mechanism influencing apoptosis in HSCs.

Example 9

Microarray Analysis of LSK Cells to Identify Differentially Expressed Genes within Consenses Congenic Interval Oligonucleotide arrays of LSK cells were performed by the Microarray Facility Center at the University of Kentucky. Briefly, total RNA were extracted from at least 550,000 sorted LSK cells from a minimum of 40 mice using RNeasy® Kit (QIAGEN, Valencia, Calif.). The extracted RNA was reverse transcribed into cDNA, which was subsequently used to synthesize biotin-labeled cRNA. The labeled cRNA was then fragmented and hybridized to the Mouse Genome U74Av2 chips (MGUAv2, Affymetrix, Santa Clara, Calif.). The genechips were then washed, stained, and subsequently scanned for quantification of gene expression. Three independent biological samples were obtained for each strain and each was run on an individual chip. The gene expression levels were compared among all 4 strains using one way-ANOVA with a statistical cutoff of $P<0.05$. The genes that were differentially expressed were screened for genomic location and function of the gene products.

Oligonucleotide arrays were utilized to screen for genes in the consensus congenic interval whose differential expression may account for the observed phenotypic variations. LSK cells were sorted from bone marrow of the reciprocal congenic mice, and the two background strains mice. Large independently sorted biological samples for total RNA extraction were used to avoid representational skewing of low abundance mRNAs that may accompany amplification by PCR. Triplicate RNA samples, each independently obtained from at least 550,000 LSK cells sorted and pooled from a minimum of 40 mice, were collected from the four strains. Each RNA sample (4 strains×3 replicates=12 in all) was hybridized to an individual microarray chip (MGU Av2 Affymetrix). Results obtained from the triplicate chips for each strain were analyzed using Affymetrix Microarray Suite™ software, and were compared using one-way ANOVA for each congenic-background strain pair. The number of genes differentially expressed between B.D Chr3 and B6 strains was 96 ($P<0.05$) and between D.B Chr3 and D2 strains was 84 ($P<0.05$). Because congenic intervals represent less than 1% of the entire genome, these numbers are commensurate with the 940 differentially expressed genes measured between B6 and D2 LSK cells in these experiments.

Table 4 is a list of genes differentially expressed in reciprocal Chr 3 congenic and B6, D2 HSCs, as shown below. In Table 4, only 17 genes on 11 different chromosomes were mutually inclusive in comparisons between the reciprocal congenics and their respective background strains. Of 17 differentially expressed genes, the D2 and B6 alleles had opposite effects on transcription in 9/17. 4/17 were mapped to Chr 3, but only 1/4 was located in the consensus congenic interval, near the marker of highest linkage in the mapping (D3Mit5). The gene was identified to be latexin (Lxn), whose expression was upregulated by B6 alleles and down-regulated by D2 alleles, a pattern suggested by the linkage analysis.

TABLE 4

Genes differentially expressed in reciprocal Chr 3 congenic and B6, D2 HSCs.

| Probe Set | Gene title | Gene symbol | Chromosomal location (Mb) | Entrez gene ID | 1. Molecular function |
|---|---|---|---|---|---|
| 101209_at | Fc receptor, IgE, high affinity I, alpha polypeptide | Fcer1a | 1 (173) | 14125 | Receptor activity; IgE binding |
| 102260_at # | Growth factor independent 1B | Gfi1b | 2 (28) | 14582 | ATP binding |
| 96065_at # | Latexin | Lxn | 3 (67) | 17035 | Enzyme inhibitor activity Metalloendopeptidase inhibitor activity |
| 92770_at * | S100 calcium binding protein A6 (calcyclin) | S100a6 | 3 (91) | 20200 | Calcium ion binding; Protein binding Growth factor activity |
| 98600_at # | S100 calcium binding protein A11 (calizzarin) | S100a11 | 3 (93) | 20195 | Cytokine activity; Calcium ion binding |
| 103257_at | RIKEN cDNA 4930577M16 gene (transmembrane protein 56) | 4930577 M16Rik (Tmem56) | 3 (121) | 99887 | Unknown |
| 94559_at | General transcription factor III A | Gtf3a | 5 (145) | 66596 | DNA binding |
| 102011_at | RIKEN cDNA 2610507L03 gene | 2610507L03Rik | 7 (23) | 72140 | Unknown |
| 94286_at | RIKEN cDNA 9130011J15 gene | 9130011J15 Rik | 8 (71) | 66818 | Unknown |
| 93498_s_at # | Amyloid beta (A4) precursor-like protein 2 | Aplp2 | 9 (31) | 11804 | DNA binding; Protein binding Serine-type endopeptidase inhibitor activity |
| 101026_at * | Pituitary tumor-transforming 1 | Pttg1 | 11 (43) | 30939 | Cysteine protease inhibitor activity |
| 16128_at # | MYB binding protein (P160) 1a | Mybbp1a | 11 (72) | 18432 | Protein binding Transcriptional represser activity |
| 93134_at | Neuronal pentraxin 1 | Nptx1 | 11 (119) | 18164 | Calcium ion binding |
| 100391_at | Mitogen activated protein kinase 8 | Mapk8 | 14 (29) | 26419 | Kinase activity; Transferase activity |
| 100343_at * | Tubulin, alpha 1 | Tuba1 | 15 (99) | 22142 | GTPase activity; GTP binding Structural constituent of cytoskeleton |
| 103282_at * | RAS, guanyl releasing protein 2// similar to calcium and DAG-regulated guanine nucleotide exchange factor I | Rasgrp2// LOC381240 | 19 (6) | 19395// 381240 | Guanyl-nucleotide exchange factor activity Calcium ion binding; Diacylglycerol binding Kinase activity |
| 160391_at | Fatty acid desaturase 1 | Fads1 | 19 (9) | 76267 | Linoleoyl-CoA desaturase activity Oxidoreductase activity |

Total RNA isolated from LSK cells in B.D Chr3, D.B Chr3 congenic, and B6, D2 mice was reverse transcribed into cDNA and subsequently used for the synthesis of cRNA. cRNA was labeled with biotin and hybridized onto Affymetrix Mouse Genome U74Av2 chip. Gene expression inLSK cells was quantified and averaged from 3 independent experiments. The gene expression levels were compared between congenic and repective background mice using one way-ANOVA with a statistical cutoff of p < 0.05. 17 genes are differentially expressed among all 4 strains.
indicates the genes whose expression is up-regulated by the B6 alleles (high expression in D.B Chr3 and B6 cells) but down-regulated by the D2 alleles (low expression in B.D Chr3 and D2 cells), whereas * indicate the genes whose expression is upregulated by the D2 alleles but down-regulated by the B6 alleles.

Example 10

Determination of Lxn mRNA Levels in Hematopoietic Cells

Figure 6A:
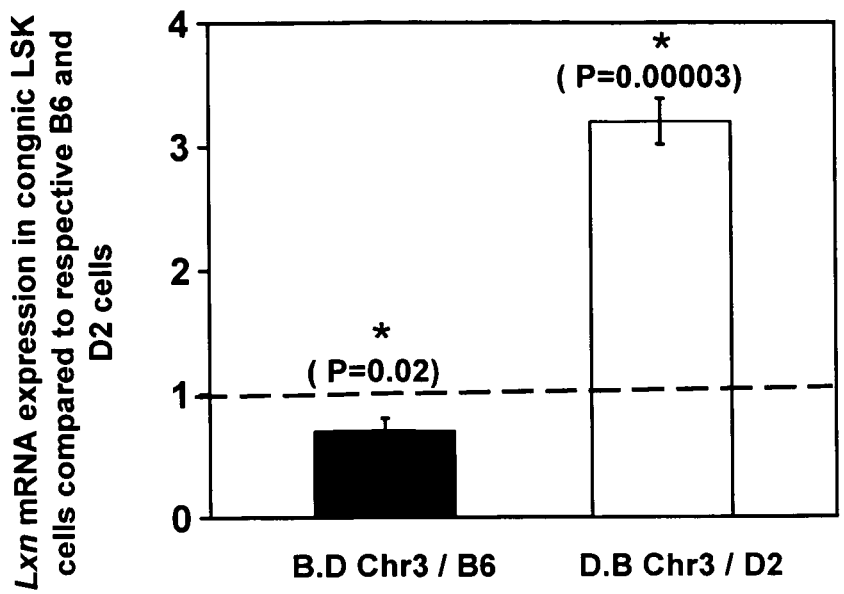
FIG. 6A illustrates Lxn mRNA expression in congenic LSK cells compared with B6 and D2 cells, as described in Example 10.

FIG. 6A illustrates Lxn mRNA expression in congenic LSK cells compared with B6 and D2 cells. In FIG. 6A, an inverse relationship between Lxn expression and the number of CAFC day 35 is observed, which confirms the microarray results both qualitatively and quantitatively. As predicted, B6 alleles in the congenic interval increased Lxn transcripts by around 3-fold in LSK cells (P=0.00003), and reduced CAFC day 35 numbers by more than half. In contrast, D2 alleles significantly decreased Lxn expression (P=0.02) and increased HSC numbers observed in FIG. 6A. Identical number ($2 \times 10^5$) of LSK cells were sorted from each strain and Lxn mRNA level in these cells was quantified by real-time PCR and compared between congenic and respective background mice. Results are the average ($\pm 1$ SD) of 12 measurements derived from 3 independent biological examples.

Example 11

Figure 6B:
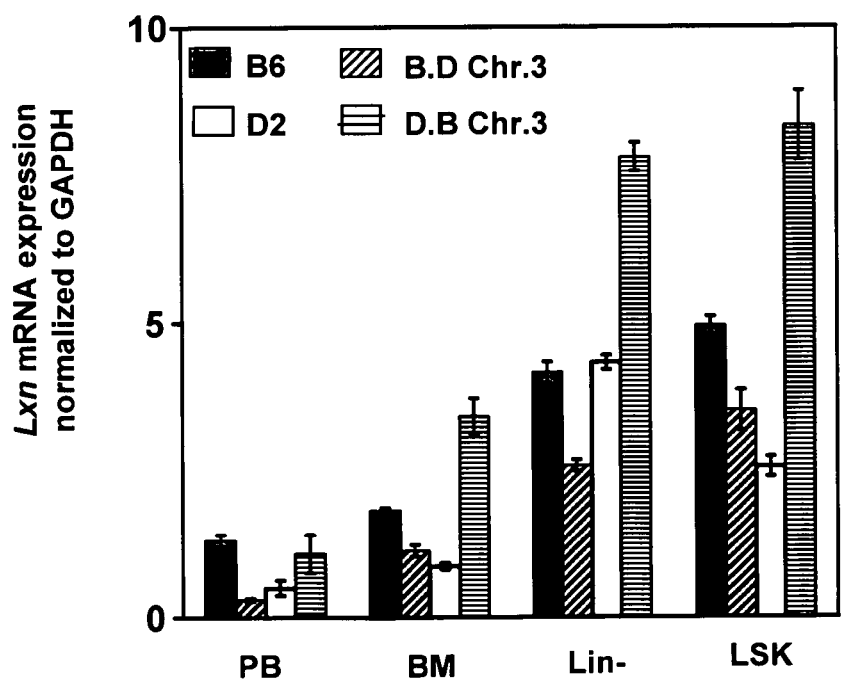
FIG. 6B illustrates quantitation of Lxn transcripts by real-time PCR in peripheral blood leukocytes, whole bone marrow, Lin-negative bone marrow cells, and LSK stem cells, as described in Example 11.

Lxn Expression in Undifferentiated and Differentiated Hematopoietic Cell Populations Lxn expression levels were determined along the differentiation pathway in the hematopoietic system. FIG. 6B illustrates quantitation of Lxn transcripts by real-time PCR in peripheral blood leukocytes, whole bone marrow, Lin-negative bone marrow cells, and LSK stem cells. In FIG. 6B, the same number of peripheral blood leukocytes, whole bone marrow, Lin-negative bone marrow cells, and LSK stem cells in each of the four strains were evaluated. Two points are noteworthy from the compiled results of three independent experiments. First, overall levels of Lxn expression per cell in each of the populations increase in concert with the content of primitive hematopoietic cells. Second, Lxn expression per cell in each of the cell populations accurately reflects the presence of B6 (higher expression) or D2 (lower expression) alleles in the two congenic and background strains. Lxn expression in differentiated peripheral blood leukocytes (PB), bone marrow nucleated cells and primitive hematopoietic cell-enriched population, including lineage-negative cells (Lin−) and HSCs (LSK cells). Lxn mRNA level was measured by quantitative real-time PCR and shown as mean ($\pm 1$ SD) (n=12).

Quantitative real-time PCR was performed as follows. Identical numbers (200,000) of cells were used for total RNA extraction in each type of cell population (peripheral blood, bone marrow, Lin-negative and LSK cells) for each mouse strain. Isolated total RNA was reverse transcribed into cDNA using random hexamers in a TaqMan® reverse transcription solution (PN N8080234) and stored at −20° C. In real-time PCR reactions, primer and probe mix for Lxn were purchased from Applied Biosystems (Foster city, Calif., USA). Taq-Man® rodent glyceraldehyde-3-phosphate dehydrogenase (GAPDH) (PN 4308313) served as an endogenous control to normalize Lxn expression. PCR reactions were set up according to manufacturer's instructions using TaqMan® universal PCR master mix (PN 4304437). Analyses of gene expression were performed in single reporter assays in an ABI PRISM 7700 sequence detection system (PE Biosystems, Foster city, Calif., USA).

Example 12

Lxn Protein Levels in Hematopoietic Cells of Congenic and Background Strain Mice A rabbit anti-mouse LXN antibody was generated from the LXN-specific amino acid sequence CKHNSRLPKEGQAE at the carboxyl terminus. Because Lxn transcripts were present at reasonable levels in unfractionated bone marrow and in Lin-negative cells described above in FIG. 6B of Example 11, the cell lysates derived from these cells were employed for Western blot analysis.

Figure 6C:
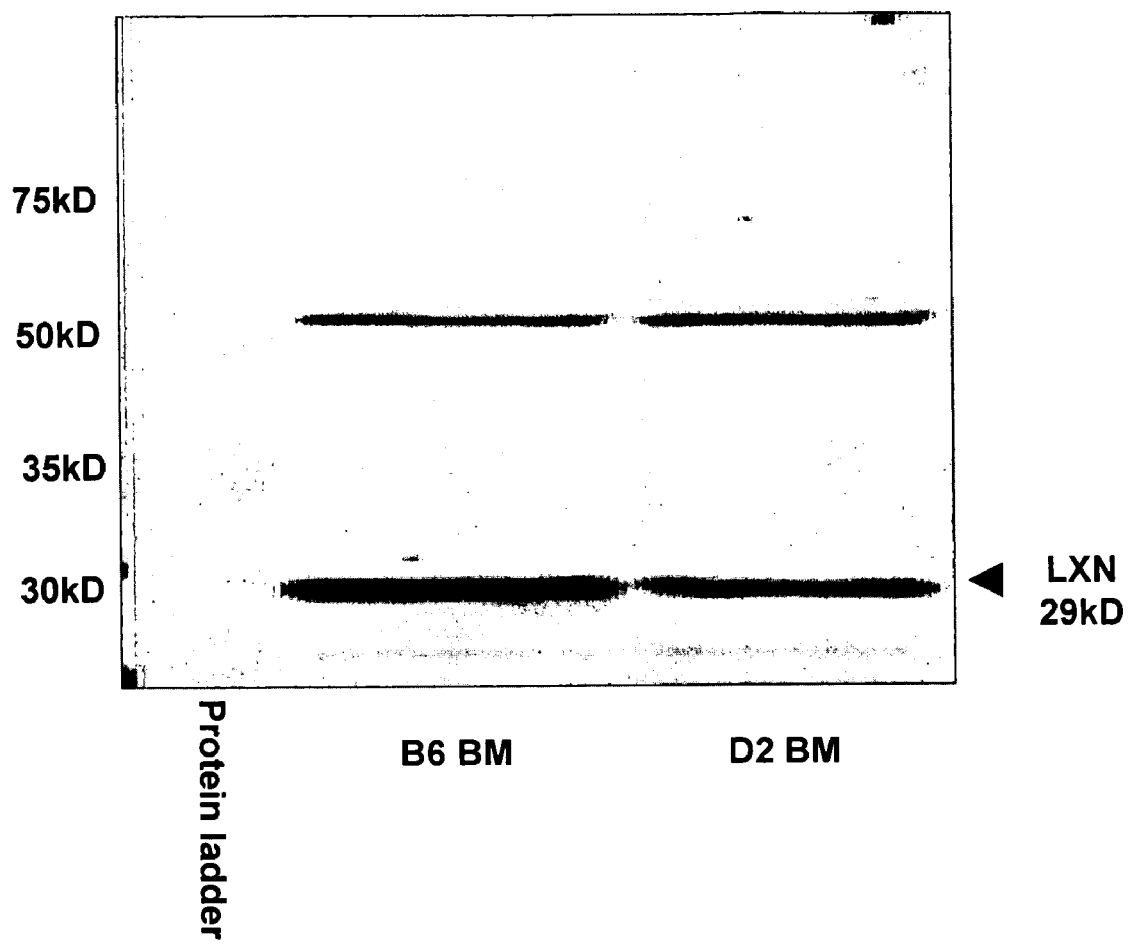
FIG. 6C illustrates immunoreactivity between the anti-mouse LXN antibody and a protein (29 kD) from bone marrow cells by a Western Blot, as described in Example 12.

FIG. 6C illustrates immunoreactivity between the anti-mouse LXN antibody and a protein (29 kD) from bone marrow cells by a Western Blot. In FIG. 6C, LXN protein (29 kDdk) was detected by the anti-lLXN antibody using extracts prepared from B6 and D2 BM samples. Rabbit anti-mouse lLXN polyclonal Ig-G antibody was generated from the Lxn-specific amino acid sequence at the carboxyl terminus.

Figure 6D:
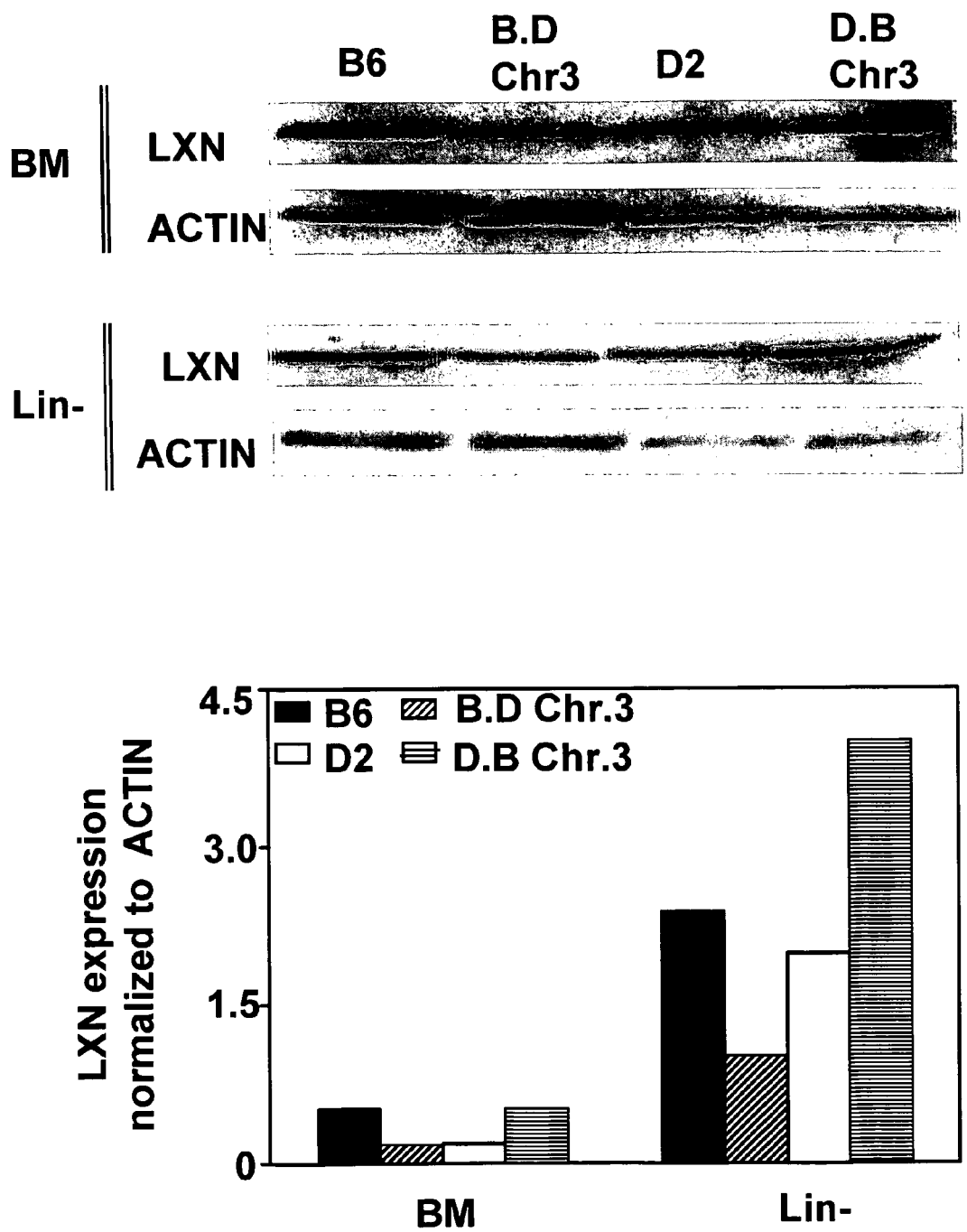
FIG. 6D illustrates the levels of LXN protein in whole bone marrow and Lin-negative cells, as described in Example 12.

FIG. 6D illustrates the levels of LXN protein in whole bone marrow and Lin-negative cells. Consistent with the real-time PCR results, Lin-negative cells contain more LXN than bone marrow cells. The cellular content of LXN in both whole bone marrow and Lin-negative cells was significantly higher in mouse strains with B6 alleles at and around the Lxn locus. The effects of both B6 and D2 Lxn alleles had more prominent effects on either increasing or decreasing Lxn expression, respectively, when present on opposite strain background than in the native context. These results suggest an influence of other loci acting through epistatic interactions to optimize Lxn expression in the two strains. Western blot was performed on BM nucleated and Lin– cells. The blots (left) and their quantification (right) profiles demonstrate the differential expression of Lxn protein in congenic and B6, D2 mice. Actin is used as the control. The blots are from one representative analysis out of 4 independent experiments.

Western blots were performed as follows. Cell samples were lysed at a concentration of $2 \times 10^7$ cells/ml in protein lysis buffer containing: 10 mM Tris pH7.5, 50 mM NaCl, 30 mM sodium pyrophosphate, 50 mM NaF, 5 µM $ZnCl_2$ and 1% Triton X-100, 2.8 ug/ml aprotinin (Sigma), 1 mM phenylmethylsulfonyl fluoride (Sigma), 1 mM sodium vanadate ($Na_3VO_4$) 1 µg/ml pepstatin, and 1 µg/ml leupeptin (Oncogene Research, Mass., USA). Lysate was incubated on ice for 30 min, and then centrifuged at 15,000× g for 10 minutes to remove debris. The resulting supernatant was then aliquoted and stored at −80° C. For Western blot, protein lysates were thawed and mixed with running buffer and a reducing agent (Novex, San Diego, Calif., USA, per manufacturer's instructions) and heated at 95° C. for 5 minutes. Samples were then analyzed by denaturing PAGE (Novex, 10% bis-Tris gel) using the equivalent of $4 \times 10^5$ cells per lane. Following electrophoresis, samples were electro-transferred onto immunobilon-P membranes (Millipore, Bedford, Mass., USA), which were subsequently blocked and probed with polyclonal rabbit anti-Lxn Ig-G antibody at a 1:3000 dilution. This antibody was generated from the Lxn-specific amino acid sequence CKHNSRLPKEGQAE at the carboxyl terminus, and was produced by Bethyl Laboratories, Inc (Montgomery, Tex.). Primary antibodies were detected using alkaline phosphatase-conjugated secondary antibodies (Santa Cruz Biotechnology) and electro-chemifluorescent (ECF) reagent (Pharmacia Biotech) according to the manufacturer's instructions. Blots were visualized using a Molecular Dynamics STORM 860 system and Imagequant Software. Following the detection and quantification of anti-Lxn antibody, immunobilon-P membrane was sequentially stripped in 40% methanol and the buffer containing 100 mm β-mercaptoethanol, 2% sodium dodecyl sulfate and 62.4 mM Tris-HCl to remove ECF reaction product and antibodies, respectively. The stripped membrane was re-probed with anti-actin antibody (Sigma) at 1:500,000 dilution and detected as described previously.

Example 13

Cis-Regulation of Lxn Expression

Because Lxn expression was detected and quantified in LSK cells of the 30 BXD RI strains in the GeneNetwork database, a linkage analysis to search for a QTL that could modify Lxn expression was performed. When modifiers of Lxn expression were queried using such an approach, suggestive linkage (LRS>9.6) was obtained to a genomic interval spanning from 56.9 Mb to 66.8 Mb on Chr 3, very close to the genomic locations of D3Mit5 and Lxn, a finding consistent with cis-regulation. Moreover, the negative additive effects of all markers in this genomic interval suggest that the B6 allele increases Lxn expression, which corroborates our results from microarray, real-time PCR, and Western blot analyses. Therefore, these results not only suggest the existence of a regulatory element in the upstream region of the Lxn sequence, but also corroborate D3Mit5 as a marker, presumably the primary one, for a QTL directly or indirectly responsible for the phenotypes conferred by the Chr 3 QTL.

Figures 7A, 7B:
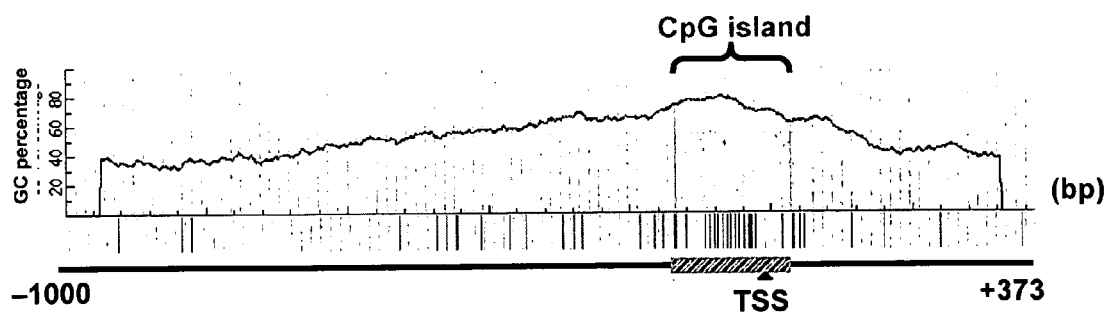
FIG. 7A illustrates various QTLs that may be involved in the regulation of Lxn expression, as described in Example 13.
FIG. 7B illustrates a CpG island analysis in the upstream sequence of Lxn open-reading frame, as described in Example 13.

FIG. 7A illustrates various QTLs that may be involved in the regulation of Lxn expression. In FIG. 7A, a linkage analysis was performed on GeneNetwork to search for a QTL that affects Lxn expression. A genomic region on Chr 3 ranging from 56.9 Mb to 66.8 Mb is shown to be associated with the Lxn expression with suggestive LRS values (between gray and pink lines). The linked QTL are listed with corresponding LRS score and additive effect. The single nucleotide polymorphism (SNPs) across Chr 3 are shown as tick marks on the X-axis.

FIG. 7B illustrates a CpG island analysis in the upstream sequence of Lxn open-reading frame. Analysis of the upstream sequence of the Lxn open reading frame revealed a 164 bp CpG island. Nucleotide sequence of Lxn in upstream region (−1000 bp) and the first 3 exons (+373 bp) was obtained from Ensembl database with ID number ENSMUSG0000047557. Transcription start site (TSS) is as indicated. CpG island search using MethPrimer software showed a 164 bp region (−138 bp to +26 bp) in the upstream of Lxn sequence enriched for CpG repeats.

Thus, differential methylation status in the regulatory region of Lxn may be involved in the differential expression of Lxn. The results also suggest that Lxn may be a potential "tumor progenitor gene" which plays an occult role in early stages of cancer development. Taken together, each of these possible pathways may be synergistically or independently involved in the regulation of cycling, apoptosis, and/or self-renewal of HSCs with entrained consequences for its population size.

Example 14

A Decrease in Stem Cell Numbers by the Overexpression of Lxn

Because D2 and B.D Chr3 congenic mice have lower levels of Lxn expression and higher stem cell numbers, Lxn expression in both strains were enhanced in both strains to test the effect of Lxn overexpression on stem cell numbers.

Figure 8A:
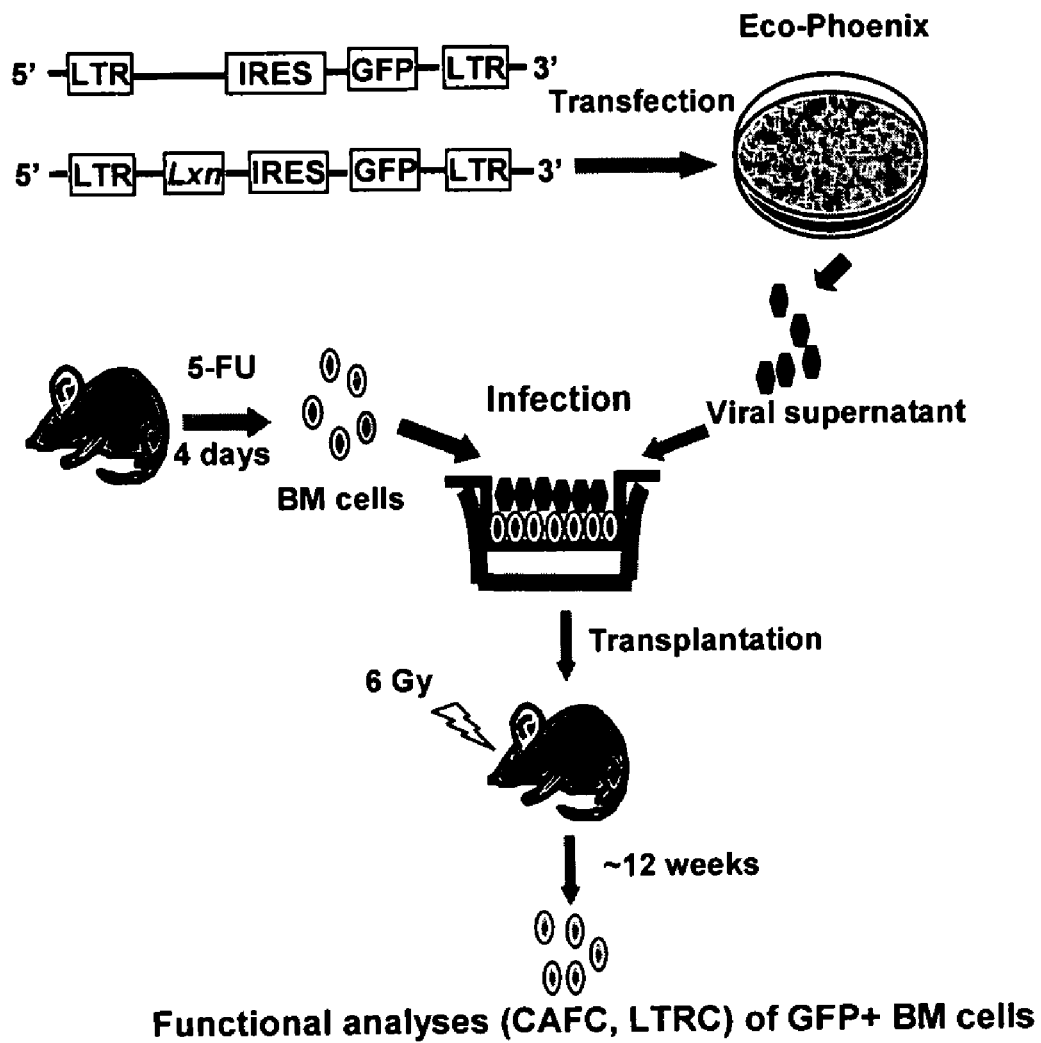
FIG. 8A illustrates a schematic for in vitro infection of bone marrow cells with retroviral vectors containing either GFP or Lxn (Lxn-GFP), and subsequent transplantation into irradiated mouse recipients, as described in Example 14.

FIG. 8A illustrates a schematic for in vitro infection of bone marrow cells with retroviral vectors containing either GFP or Lxn (Lxn-GFP), and subsequent transplantation into irradiated mouse recipients. At ≧12 weeks following transplant, when all hematopoiesis originated from transplanted stem cells, the bone marrow was harvested from the primary recipients and cells expressing GFP were sorted using flow cytometry. The GFP-positive population was isolated to be assayed for CAFC day 35 content in D2-derived cells and for LTRC frequency in B.D Chr3-derived cells. In FIG. 8A, the structure of Lxn-containing retroviral vector is shown in which the Lxn-GFP represents the Lxn-containing vector; GFP represents the no insert control.

Figure 8B:
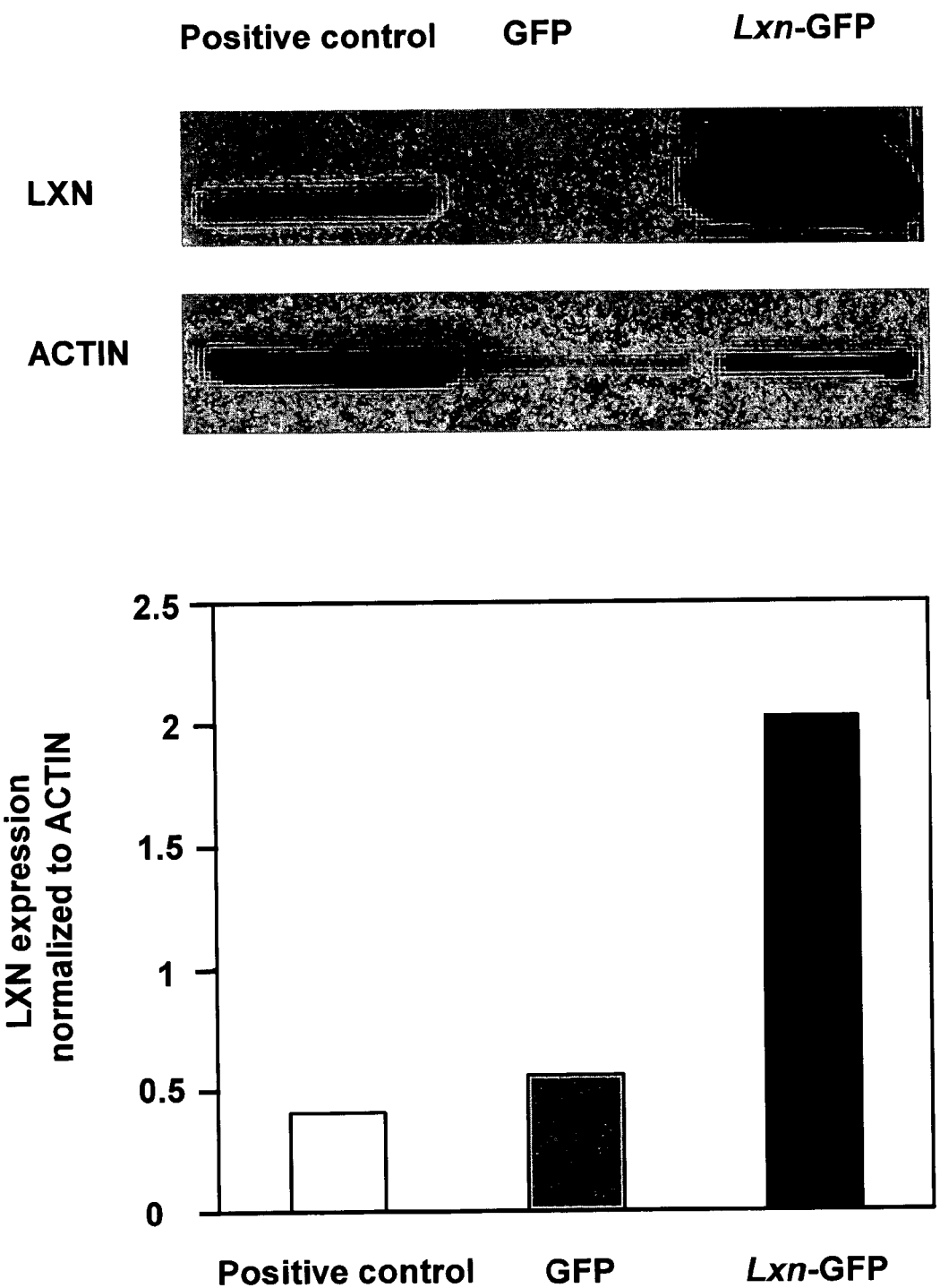
FIG. 8B illustrates results of a Western blot analysis of GFP+ cells sorted from the BM of the recipient mice transplanted with either Lxn-GFP or GFP-transduced cells, as described in Example 14.

FIG. 8B illustrates results of a Western blot analysis of GFP+ cells sorted from the BM of the recipient mice transplanted with either Lxn-GFP or GFP-transduced cells. Expression levels of Lxn protein in bone marrow cells transduced with Lxn-GFP were higher than the expression levels of GFP-transduced cells, confirming that both Lxn transcript and protein levels were dramatically increased in Lxn-GFP cells.

Figure 8C:
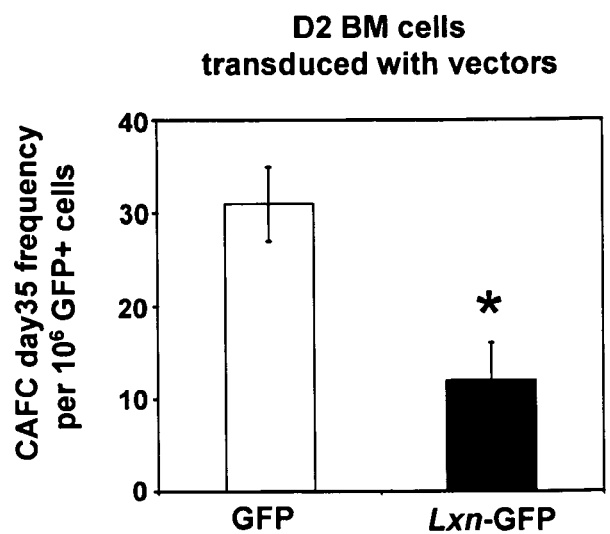
FIG. 8C illustrates results of CAFC day 35 frequency assay of D2 bone marrow cells transduced with either GFP control or Lxn-GFP, as described in Example 14.

FIG. 8C illustrates results of CAFC day 35 frequency assay of D2 bone marrow cells transduced with either GFP control or Lxn-GFP. * P=0.0059 (t-test, one-tail).

Figure 8D:
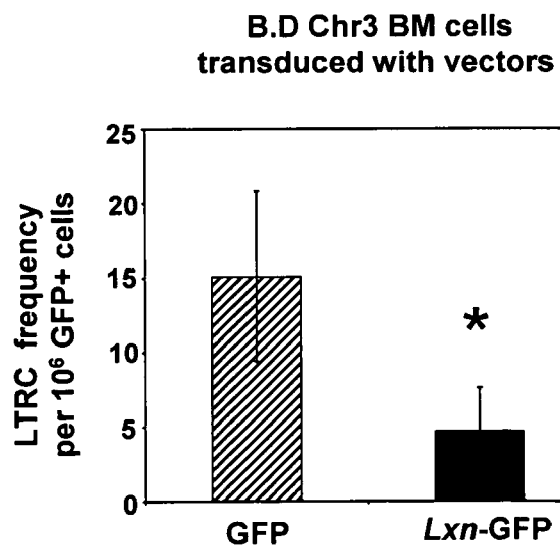
FIG. 8D illustrates results of long-term repopulating cells (LTRC) frequency assay of B.D Chr.3 congenic BM cells transduced with either GFP control or Lxn-GFP, as described in Example 14.

FIG. 8D illustrates results of long-term repopulating cells (LTRC) frequency assay of B.D Chr.3 congenic BM cells transduced with either GFP control or Lxn-GFP. * P=0.0458 (t-test, one-tail).

In FIGS. 8C-8D, the frequency of primitive stem cells was significantly reduced (P<0.05) in the population infected with the Lxn-GFP vector relative to cells infected with the GFP control vector. Approximately a 3-fold decrease in HSC numbers in Lxn-overexpressing cells reflects precisely the difference between two parental B6 and D2 strains. Therefore, these results further confirm Lxn as the primary quantitative gene negatively regulating HSC numbers.

Retroviral vectors were constructed as follows. The retroviral vector, Sfbeta 91, served as a control and the backbone for cloning of Lxn cDNA. It contained the 5'-long terminal repeat (LTR) derived from myeloproliferative sarcoma virus (MPSV) and a 3'-LTR derived from spleen focus forming virus (SFFV). The internal ribosomal entry site sequence derived from the encephalomyocarditis virus was used for simultaneous translation of gene insert and the gene for enhanced green fluorescent protein (GFP). The Lxn cDNA sequence was cloned upstream of the IRES of the Sfbeta91 vector (MPSV-IRES-GFP-SFFV) to create a recombinant Lxn-carrying vector (MPSV-Lxn-IRES-GFP-SFFV). Production of high-titer helper-free retrovirus was carried out by standard procedure in ectotropic Phoenix packaging cells.

Infection of primary murine bone marrow cells were infected as follows. Primary mouse bone marrow cells were transduced as previously described with modifications specified below. Briefly, bone marrow cells were harvested from mice treated 4 days previously with 150 mg/kg body weight 5-fluorouracil (5-FU) (Sigma, St. Louis, Mo.) and cultured for 24 hours in Dulbecco's modified eagle's medium (DMEM) supplemented with 10% fetal bovine serum (FBS), 1% penicillin/streptomycin (Gibco Technologies, Carlsbad, Calif.), 50 ng/mL recombinant mouse stem cell factor (mSCF), 10 ng/mL mouse interleukin 6 (mIL-6), and 10 ng/mL mouse interleukin 3 (mIL-3) (R&D Systems, Minneapolis, Minn.). The cells were then harvested and slowly spread on the top surface of the membrane of a Transwell insert (Corning Incorporated Life Sciences, Acton, Mass.) at a density of $2 \times 10^6$ cells per well. The viral supernatants were added to the Transwell inserts along with 4 μg/ml of polybrene and were cultured with cells for further 48 hours. The viral supernatant was changed 3 times during this period of time. The recovered cells were then transplanted into sublethally-irradiated (600 Rad) recipient mice at a dose of at least $1 \times 10^6$ cells per mouse. Around 12 weeks after transplantation, retrovirally-transduced, i.e. GFP positive, bone marrow cells were flow cytometrically sorted from primary recipient mice using a FACSVantage (Becton-Dickinson) and used for CAFC assay and limiting-dilution competitive repopulation assay.

Functional analysis of retrovirally-transduced cells were performed as follows. Identical numbers of bone marrow cells transduced with either the GFP control vector or the Lxn-GFP vector were sorted from the primary recipient mice. The CAFC and limiting-dilution competitive repopulation assays of these GFP positive cells was performed as described above. The HSC frequencies (CAFC day 35 and LTRC) were calculated and compared to measure the effects of Lxn overexpression on HSC number.

Example 15

Inhibition of Latexin by Exemplary SiRNAs

Figure 9A:
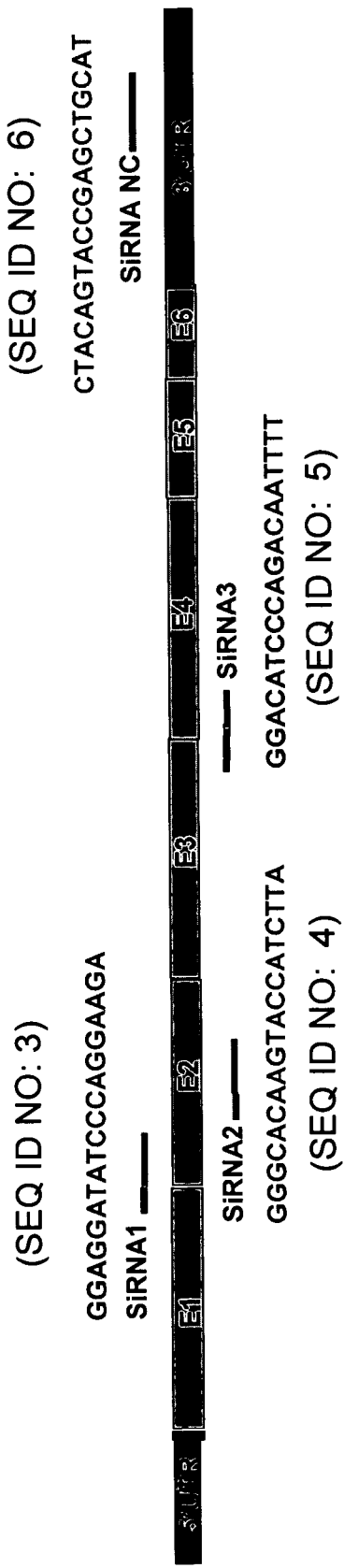
FIG. 9A illustrates exemplary SiRNAs transfected into NIH3T3 cells, as described in Example 15.
Figure 9B:
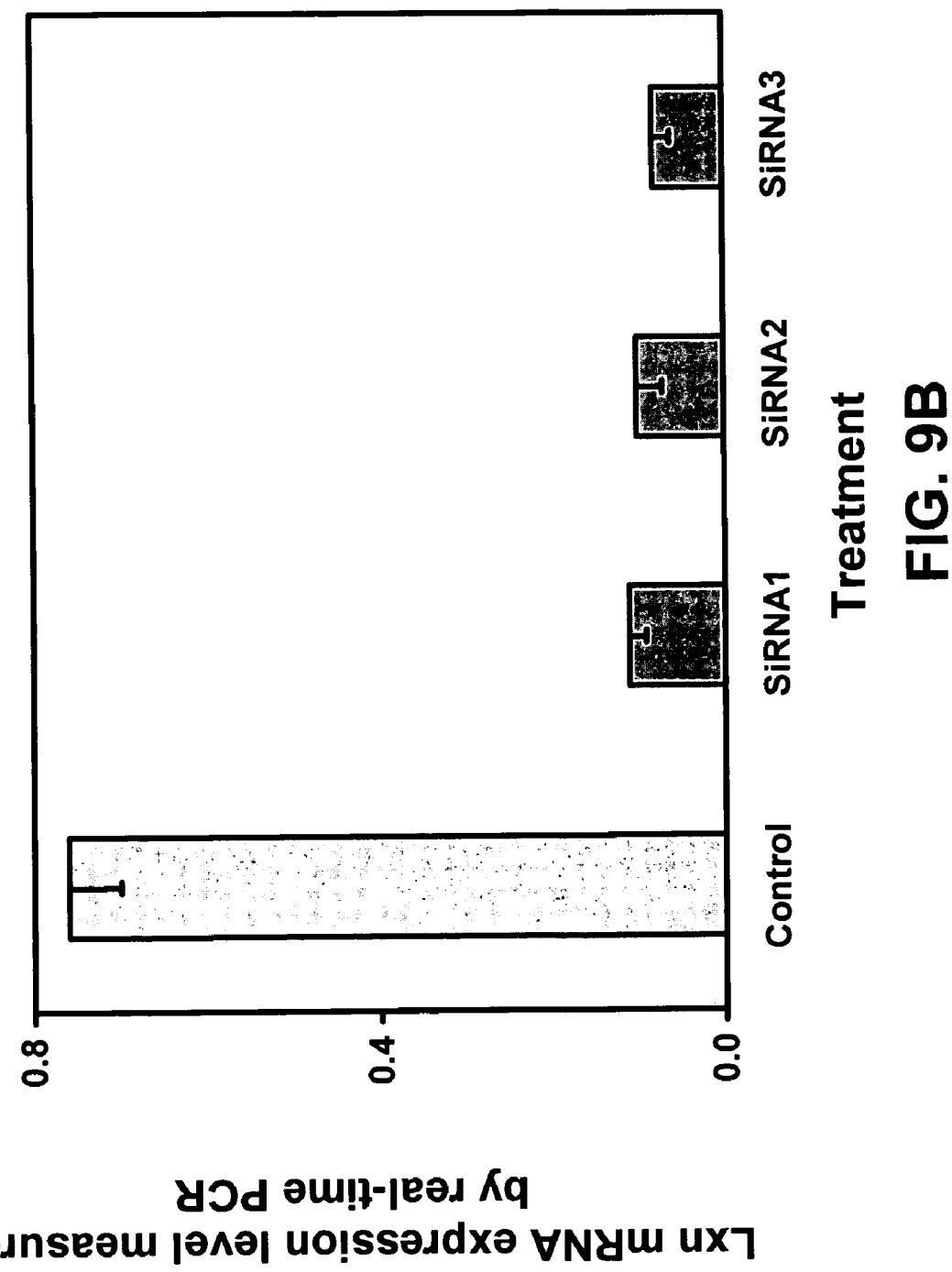
FIG. 9B illustrates the results of sequence-specific SiRNA-mediated inhibition of latexin mRNA expression in mouse adult stem cells that resulted in HSC proliferation and HSC apoptotic inhibition, as described in Example 15.

FIG. 9A illustrates exemplary SiRNAs transfected into NIH3T3 cells, as described in Example 15. FIG. 9B illustrates the results of sequence-specific SiRNA-mediated inhibition of latexin mRNA expression in mouse adult stem cells that resulted in HSC proliferation and HSC apoptotic inhibition, as described in Example 15. For latexin-specific inhibition, three exemplary SiRNA were ordered from Ambion (Austin, Tex.) identified by the following IDs: SiRNA1 (724142) designated as SEQ ID NO:3 (5'-UCUUCCUGGGAUAU CCUCC-3'); SiRNA2 (72510) designated as SEQ ID NO:4 (5'-UAAGAUGGUACUUGUG CCC-3'); and SiRNA3 (72605) designated as SEQ ID NO:5 (5'-AAAAUUGU-CUGGGAUGUC C-3'). A sequence in 3' untranslated region was used as a negative control "SiRNA NC" designated as SEQ ID NO:6 (5'-AUGCAGCUCGGUACUGUAG-3'). For each type of SiRNA, the sense and anti-sense RNA oligonucleotides were diluted to 200 uM concentration. For the annealing reaction, 40 ul of each oligonucleotide were mixed with 20 ul of annealing buffer (Ambion) and heated for 1 minute at 90° C., followed by an incubation for 1 hour at 37° C. For the transfection, the double-stranded RNA oligonucleotides were further diluted at 20 pmol/ul concentration. For the transfection of NIH3T3 cells with SiRNA and reported GFP plasmid, approximately $4 \times 10^5$ NIH3T3 cells were seed in a 6-well plate and were grown overnight in Iscove's Modified Dulbecco's Medium (IMDM) (Invitrogen) containing 10% fetal bovine serum (FBS). The cells were 80-90% confluent at the time of transfection. For each transfection/well, approximately 9 ul Lipofectamine™ 2000 (Invitrogen) were diluted with 250 ul Opti-MEM I Reduced Serum Medium (Gibco) and incubated for 5 minutes at room temperature. Approximately 2 ug of reporter GFP plasmid and 200 pmol of SiRNA were also diluted in 250 ul of Opti-MEM I Reduced Serum Medium. The diluted Lipofectamine™ 2000 were combined with the diluted SiRNA and the reporter plasmid. The mixture was incubated for 20 minutes at room temperature. The NIH3T3 cells were washed twice with PBS (Invitrogen) and incubated with 500 ul of RNA-reporter plasmid-Lipofectamine™ 2000 complex in each well. 12~15 hours after incubation, the medium was changed to IMDM plus 10% FBS. The cells were detached by trypsin and resuspended into 5 ug/mL propidium (PI) solution. For sorting transfected (GFP+) cells, flow cytometric analysis was performed on a dual-laser FACSVantage (Becton Dickinson Immunocytometry Systems, San Jose, Calif.) to select PI negative and GFP positive cells.

Quantitative real-time PCR was performed in the following manner. Identical numbers (200,000) of cells were used for total RNA extraction in cells transfected with 3 SiRNAs and negative control RNAs. Isolated total RNA was reverse transcribed into cDNA using random hexamers in a TaqMan® reverse transcription solution (PN N8080234) and stored at −20° C. Quantitative real-time PCR analyses of selected genes were performed in single reporter assays with an ABI PRISM 7700 sequence detection system (PE Biosystems, Foster city, Calif., USA). PCR reactions were set up according to manufacturer's instructions using TaqMan® universal PCR master mix (PN 4304437), and the primer and probe mixes for each tested gene were purchased from Applied Biosystems (Foster city, Calif., USA). TaqMan® rodent glyceraldehyde-3-phosphate dehydrogenase (GAPDH (PN 4308313) served as an endogenous control to normalize gene expression. The analysis of gene expression was performed by the relative standard curve method. In brief, standard curves were prepared for the GAPDH control and for each of tested genes, and the amount of GAPDH control and test gene were determined from the standard curve. A normalized test gene value was determined relative to GAPDH expression. Each biological sample was obtained from at least 5 mice, and each sample was run with at least 5 replicates within an experiment. Three replicate biological experiments were performed in each strain.

It will be appreciated that, although specific embodiments of the invention have been described herein for purposes of illustration, various modifications may be made without departing from the spirit and the scope of the invention. Accordingly, the invention is not limited except as by the appended claims.

We claim:

1. An ex vivo method for producing a renewed population of hematopoietic stem cells (HSCs), the method comprising:
   obtaining a first HSC population from a donor;
   contacting the first HSC population with an antagonist that reduces the expression and/or the activity of latexin; and
   culturing the HSC population under in vitro conditions that promote cell proliferation and/or inhibit apoptosis to obtain a second HSC population that comprises a progeny of the first HSC population,
   wherein latexin includes a latexin polynucleotide variant and/or a latexin polypeptide variant that interacts with the antagonist.

2. The ex vivo method of claim 1, wherein obtaining the first HSC population from the donor further comprises isolating a HSC population from a mixture of cells obtained from a biopsy removed from the donor.

3. The ex vivo method of claim 1, wherein the first HSC population and the second HSC population comprise HSCs that express any of the following combination of cell surface markers:
   Thy-1$^{lo}$ Sca-1$^+$ Lineage$^-$ c-kit$^+$; or
   CD150$^+$ CD48$^-$ Sca-1$^+$ Lineage$^-$ c-kit$^+$; or
   Thy-1$^{lo}$ CD150$^+$ CD48$^-$ Sca-1$^+$ Lineage$^-$ c-kit$^+$.

4. The ex vivo method of claim 1, wherein latexin expression and/or latexin activity includes intracellular processes that regulate latexin promoter activation, transcriptional activation, transcriptional termination, post-transcriptional processing, translational initiation, translational elongation, translational termination, and post-translational modification.

5. The ex vivo method of claim 1, wherein the antagonist is selected from the group consisting of: SiRNAs, ribozymes, and anti-sense oligodeoxynucleotides.

6. The ex vivo method of claim 1, wherein the antagonist can promote HSC proliferation by at least 25%.

7. The ex vivo method of claim 1, wherein the latexin polynucleotide variant has at least 70% sequence similarity to SEQ ID NO: 1.

8. The method of claim 1, wherein the latexin polypeptide variant has at least 70% sequence similarity to SEQ ID NO: 2.

9. A method for reconstituting a recipient host with a population of hematopoietic stem cells (HSCs) generated ex vivo, the method comprising:
   obtaining a first HSC population from a donor;
   contacting the first HSC population with an antagonist that reduces the expression and/or the activity of latexin;
   culturing the HSC population under in vitro conditions that promote cell proliferation and/or inhibit apoptosis to obtain a second HSC population comprising a progeny of the first HSC population; and
   providing the second HSC population to the recipient host in need of HSC reconstitution,
   wherein latexin includes a latexin polynucleotide variant and/or a latexin polypeptide variant that interacts with the antagonist.

10. The method of claim 9, wherein the first HSC population and the second HSC population comprise HSCs that express any of the following combination of cell surface markers:
    Thy-1$^{lo}$ Sca-1$^+$ Lineage$^-$ c-kit$^+$; or
    CD150$^+$ CD48$^-$ Sca-1$^+$ Lineage$^-$ c-kit$^+$; or
    Thy-1$^{lo}$ CD150$^+$ CD48$^-$ Sca-1$^+$ Lineage$^-$ c-kit$^+$.

11. The method of claim 9, wherein the donor is the same organism as the recipient host in that the donor has identical HLA haplotype as the recipient host, and wherein the recipient host is reconstituted with autologous HSCs when provided with the second HSC population.

12. The method of claim 9, wherein the donor is not the same organism as the recipient host, and the donor has a HLA haplotype of sufficient similarity to the HLA haplotype of the recipient host, and wherein the recipient host is reconstituted with allogenic HSCs when provided with the second HSC population.

13. The method of claim 9, wherein the antagonist is selected from the group consisting of: SiRNAs, ribozymes, and anti-sense oligodeoxynucleotides.

14. The method of claim 9, wherein the antagonist can promote HSC proliferation by at least 25%.

15. The method of claim 9, wherein the latexin polynucleotide variant has at least 70% sequence similarity to SEQ ID NO: 1.

16. The method of claim 9, wherein the latexin polypeptide variant has at least 70% sequence similarity to SEQ ID NO: 2.

17. The method of claim 9, wherein the recipient host is affected with a disease of the blood, a disease of the bone marrow, a cancer of the blood, a cancer of the bone marrow, an immunological disorder, anemia, leukemia, thalassemia major, sickle-cell disease, myelodysplastic syndrome, lymphoma, aplastic anemia, and/or multiple myeloma.

* * * * *

SEQUENCE LISTING

<160> NUMBER OF SEQ ID NOS: 6

<210> SEQ ID NO 1
<211> LENGTH: 1113
<212> TYPE: DNA
<213> ORGANISM: human

<400> SEQUENCE: 1

```
agaagcagtc agcccagggc tctcggatgc agggagcctg ggcccaaaca gcagcttccg      60
gagtcggaag gagctgagga agaagacaga ctgaaggagc ttgcgacttt tccgcctcgg     120
caaccggacc cagcagcaag caggacgggc ggcgctctgc tactggtccc gttaagccaa     180
agtagcccaa gccctgaagt cactgctcat ccggaatgga aatcccgccg accaactacc     240
cagcctccag ggcggccttg gtggcacaga actacatcaa ctaccagcag gggaccccgc     300
acagggtgtt tgaggtgcag aaggtcaaac aagccagcat ggaggatatt ccaggaagag     360
gacataagta tcgccttaaa tttgctgttg aagaaattat acaaaaacaa gttaaggtga     420
actgcacagc tgaagtactt tacccttcaa cgggacaaga aactgcacca gaagtcaact     480
tcacatttga aggagaaact ggaaagaatc cagatgaaga agacaacaca ttttatcaaa     540
gacttaagtc catgaaggaa ccgctagaag cacaaaatat tccagacaat tttggaaatg     600
tatctccaga aatgacgctc gttctacatt tagcctgggt tgcctgtggt tatataatat     660
ggcaaaattc tactgaagac acatggtata aaatggtaaa aattcaaact gtcaagcaag     720
tgcaaagaaa tgatgacttt attgaattag actacaccat tctacttcat aatatagcat     780
ctcaggagat tattccctgg caaatgcaag ttctctggca tccacaatac ggcactaaag     840
taaaacataa tagccgtctg ccaaaggaag tacaactgga ataaacaaaa accctaacac     900
tggaagtgta aacatgtcta ttgatgtgta tgccaatttc actggcatct agcttatgag     960
gccaaataat cccaaagtgt cactttatat aaatgtcttg attacagtat agaactttat    1020
agagtccata atacaaagta tcactacata aaaatgtctt taaaacagta atagtggtat    1080
gtatatccaa aataaaaagc ttcaatttca gcc                                 1113
```

```
<210> SEQ ID NO 2
<211> LENGTH: 222
<212> TYPE: PRT
<213> ORGANISM: human

<400> SEQUENCE: 2

Met Glu Ile Pro Pro Thr Asn Tyr Pro Ala Ser Arg Ala Ala Leu Val
1               5                   10                  15

Ala Gln Asn Tyr Ile Asn Tyr Gln Gln Gly Thr Pro His Arg Val Phe
            20                  25                  30

Glu Val Gln Lys Val Lys Gln Ala Ser Met Glu Asp Ile Pro Gly Arg
        35                  40                  45

Gly His Lys Tyr Arg Leu Lys Phe Ala Val Glu Glu Ile Ile Gln Lys
    50                  55                  60

Gln Val Lys Val Asn Cys Thr Ala Glu Val Leu Tyr Pro Ser Thr Gly
65                  70                  75                  80

Gln Glu Thr Ala Pro Glu Val Asn Phe Thr Phe Glu Gly Glu Thr Gly
                85                  90                  95

Lys Asn Pro Asp Glu Glu Asp Asn Thr Phe Tyr Gln Arg Leu Lys Ser
            100                 105                 110

Met Lys Glu Pro Leu Glu Ala Gln Asn Ile Pro Asp Asn Phe Gly Asn
        115                 120                 125

Val Ser Pro Glu Met Thr Leu Val Leu His Leu Ala Trp Val Ala Cys
    130                 135                 140

Gly Tyr Ile Ile Trp Gln Asn Ser Thr Glu Asp Thr Trp Tyr Lys Met
145                 150                 155                 160

Val Lys Ile Gln Thr Val Lys Gln Val Gln Arg Asn Asp Asp Phe Ile
                165                 170                 175

Glu Leu Asp Tyr Thr Ile Leu Leu His Asn Ile Ala Ser Gln Glu Ile
            180                 185                 190

Ile Pro Trp Gln Met Gln Val Leu Trp His Pro Gln Tyr Gly Thr Lys
        195                 200                 205

Val Lys His Asn Ser Arg Leu Pro Lys Glu Val Gln Leu Glu
    210                 215                 220

<210> SEQ ID NO 3
<211> LENGTH: 19
<212> TYPE: RNA
<213> ORGANISM: artificial sequence
<220> FEATURE:
<223> OTHER INFORMATION: mouse

<400> SEQUENCE: 3
ucuuccuggg auauccucc                                                       19

<210> SEQ ID NO 4
<211> LENGTH: 19
<212> TYPE: RNA
<213> ORGANISM: artificial sequence
<220> FEATURE:
<223> OTHER INFORMATION: mouse

<400> SEQUENCE: 4
uaagauggua cuugugccc                                                       19

<210> SEQ ID NO 5
<211> LENGTH: 19
<212> TYPE: RNA
<213> ORGANISM: artificial sequence
```

-continued

```
<220> FEATURE:
<223> OTHER INFORMATION: mouse

<400> SEQUENCE: 5
aaaauugucu gggaugucc                                                  19

<210> SEQ ID NO 6
<211> LENGTH: 19
<212> TYPE: RNA
<213> ORGANISM: artificial sequence
<220> FEATURE:
<223> OTHER INFORMATION: mouse

<400> SEQUENCE: 6
augcagcucg guacuguag                                                  19
```